United States Patent
Myers et al.

(10) Patent No.: US 11,145,397 B1
(45) Date of Patent: Oct. 12, 2021

(54) SYSTEM AND METHOD FOR AUGMENTED REALITY DETECTION OF LOOSE PHARMACY ITEMS

(71) Applicant: Express Scripts Strategic Development, Inc., St. Louis, MO (US)

(72) Inventors: Christopher M. Myers, Dublin, OH (US); Ellen E. Seeser, St. Louis, MO (US)

(73) Assignee: Express Scripts Strategie Development, Inc., St. Louis, MO (US)

( * ) Notice: Subject to any disclaimer, the term of this patent is extended or adjusted under 35 U.S.C. 154(b) by 0 days.

(21) Appl. No.: 16/779,223

(22) Filed: Jan. 31, 2020

(51) Int. Cl.
  *G16H 20/10* (2018.01)
  *G06K 9/00* (2006.01)
  *G06N 3/08* (2006.01)
  *G06T 19/00* (2011.01)

(52) U.S. Cl.
  CPC ......... *G16H 20/10* (2018.01); *G06K 9/00671* (2013.01); *G06N 3/08* (2013.01); *G06T 19/006* (2013.01)

(58) Field of Classification Search
  CPC .............. G06F 2111/18; G06F 3/0481; G06F 3/04817; G06F 9/4443; G06F 3/04847; G06F 11/3664; G06F 3/012; G06F 3/0304; G06F 3/011–015; G06F 17/0092; G06F 13/025; G06K 9/00664–00704; G06T 19/00; G06T 17/00; G06T 7/00; G06T 19/006; G06T 2215/16; H04N 5/272; H04N 2201/3245; A63F 13/10; A61J 7/02; A61J 1/03; G06M 11/00; B65D 83/04; G07F 17/0092; G07F 13/025; B65B 57/20
  See application file for complete search history.

(56) References Cited

U.S. PATENT DOCUMENTS

| | | | |
|---|---|---|---|
| 8,775,198 B2 | 7/2014 | Wiener | |
| 9,014,427 B2 * | 4/2015 | Bear | A61J 7/0481 382/103 |
| 10,187,593 B2 | 1/2019 | Holmes | |
| 2008/0306761 A1 | 12/2008 | George | |
| 2010/0096293 A1 | 4/2010 | Liebermann | |
| 2011/0307270 A1 | 12/2011 | Berkelhamer | |
| 2013/0293580 A1 | 11/2013 | Spivack | |
| 2013/0315486 A1 * | 11/2013 | Franz | G01N 35/1016 382/190 |
| 2014/0058555 A1 | 2/2014 | Rhoads, Jr. | |
| 2014/0304156 A1 * | 10/2014 | Geller | G06Q 20/18 705/43 |

(Continued)

*Primary Examiner* — Todd Buttram
(74) *Attorney, Agent, or Firm* — Dickinson Wright PLLC

(57) ABSTRACT

A method includes capturing, by an image-capturing device, a one or more images of at least a portion of a pharmacy workstation. The method also includes identifying, by a processor in communication with the image capturing device, objects of interest in a first image of the one or more images and classifying, by the processor, the detected objects of interest using a convolutional neural network associated with the processor. The method also includes identifying, by the processor, a boundary defining an opening of a container in a second image of the one or more images. The method also includes updating, by the processor, an objects in container list based on a determination that at least one of the classified objects passed the boundary.

27 Claims, 10 Drawing Sheets

(56) References Cited

U.S. PATENT DOCUMENTS

| | | | |
|---|---|---|---|
| 2015/0302255 A1* | 10/2015 | Gershtein | G06K 9/00 |
| | | | 382/128 |
| 2018/0174292 A1* | 6/2018 | Takamori | G16H 20/10 |
| 2018/0286031 A1* | 10/2018 | Yuyama | G06T 7/0002 |
| 2018/0326149 A1 | 11/2018 | Lipschultz | |
| 2019/0110007 A1 | 4/2019 | Holmes | |
| 2019/0122103 A1* | 4/2019 | Gao | G06N 3/04 |
| 2019/0333618 A1 | 10/2019 | Tribble | |
| 2020/0050259 A1 | 2/2020 | Lam | |
| 2020/0214642 A1* | 7/2020 | Lin | G16H 30/40 |
| 2020/0242752 A1* | 7/2020 | Kakishita | G01N 21/17 |

\* cited by examiner

SYSTEM AND METHOD FOR AUGMENTED REALITY DETECTION OF LOOSE PHARMACY ITEMS

TECHNICAL FIELD

This disclosure relates to pharmacy item detection and in particular, to detecting loose pharmacy items using augmented reality.

BACKGROUND

Pharmacists and pharmacy technicians typically receive requests to fulfill pharmacy orders that include various pharmacy items. The pharmacy items may include medicine, medicine accessories, or other suitable items. In order to fulfill the pharmacy order, pharmacy technician (e.g., or the pharmacist) retrieves the items of a pharmacy order from a stockroom and brings the items to a workstation where the pharmacy technician will fulfill the pharmacy order, which may include counting quantities, generating labels, packaging items in a container, and the like.

Typically, such items in the stockroom are stored in bulk quality. Accordingly, when the pharmacy technician retrieves the items from the stockroom, the pharmacy technician typically determines how many of each of the items are required to fulfill the pharmacy order. The pharmacy technician may then update corresponding inventory lists in to indicate the inventory quantities remaining after the pharmacy technician fulfills the pharmacy order. In addition, after the pharmacy technician prepares the items for the pharmacy order, the items in the pharmacy order are typically verified, usually by a pharmacist. Such manual retrieval of stock items, inventory management, and verification can be cost and resource intensive and may be prone to human error.

SUMMARY

This disclosure relates generally to pharmacy item detection.

An aspect of the disclosed embodiments is a method for fulfilling a pharmacy order. The method includes capturing, by an image-capturing device, a one or more images of at least a portion of a pharmacy workstation. The method also includes identifying, by a processor in communication with the image capturing device, objects of interest in a first image of the one or more images and classifying, by the processor, the detected objects of interest. The objects in the one or more images may be classified using a convolutional neural network associated with the processor. The method also includes identifying, by the processor, a boundary defining an opening of a container in a second image of the one or more images. The method also includes updating, by the processor, an objects in container list based on a determination that at least one of the classified objects passed the boundary.

Another aspect of the disclosed embodiments is an augmented reality apparatus for fulfilling a pharmacy order. The augmented reality apparatus includes an image-capturing device, a processor, and a display device. The image-capturing device is configured to capture video data that includes a one or more images of at least a portion of a pharmacy workstation. The processor in communication with at least one memory that includes instructions that, when executed by the processor, cause the processor to: read a first image of the one or more images of the video data; identify objects of interest in the first image; classify the detected objects of interest (e.g., using a convolutional neural network); identify a boundary defining an opening of a container in a second image of the one or more images; update an objects in container list based on a determination that at least one of the classified objects passed the boundary; and generate information corresponding to the pharmacy order based on, at least, the objects in container list. The display device is configured to display the information.

Another aspect of the disclosed embodiments is a system for fulfilling a pharmacy order. The system includes a wearable augmented reality device and a machine learning device (e.g., convolutional neural network). The wearable augmented reality device is configured to: capture video data that includes a one or more images of at least a portion of a pharmacy workstation; identify objects of interest in the one or more images; and identify a boundary defining an opening of a container in the one or more images. The machine learning device (e.g., a convolutional neural network) is configured to classify the objects of interest identified by the wearable augmented reality device, wherein the wearable augmented reality device identifies, in the one or more images, classified objects of interest that pass the boundary of the container and provides, to a wearer of the wearable augmented reality device, information corresponding to the pharmacy order in response to identifying classified objects of interest that pass the boundary of the container.

These and other aspects of the present disclosure are disclosed in the following detailed description of the embodiments, the appended claims, and the accompanying figures.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1:
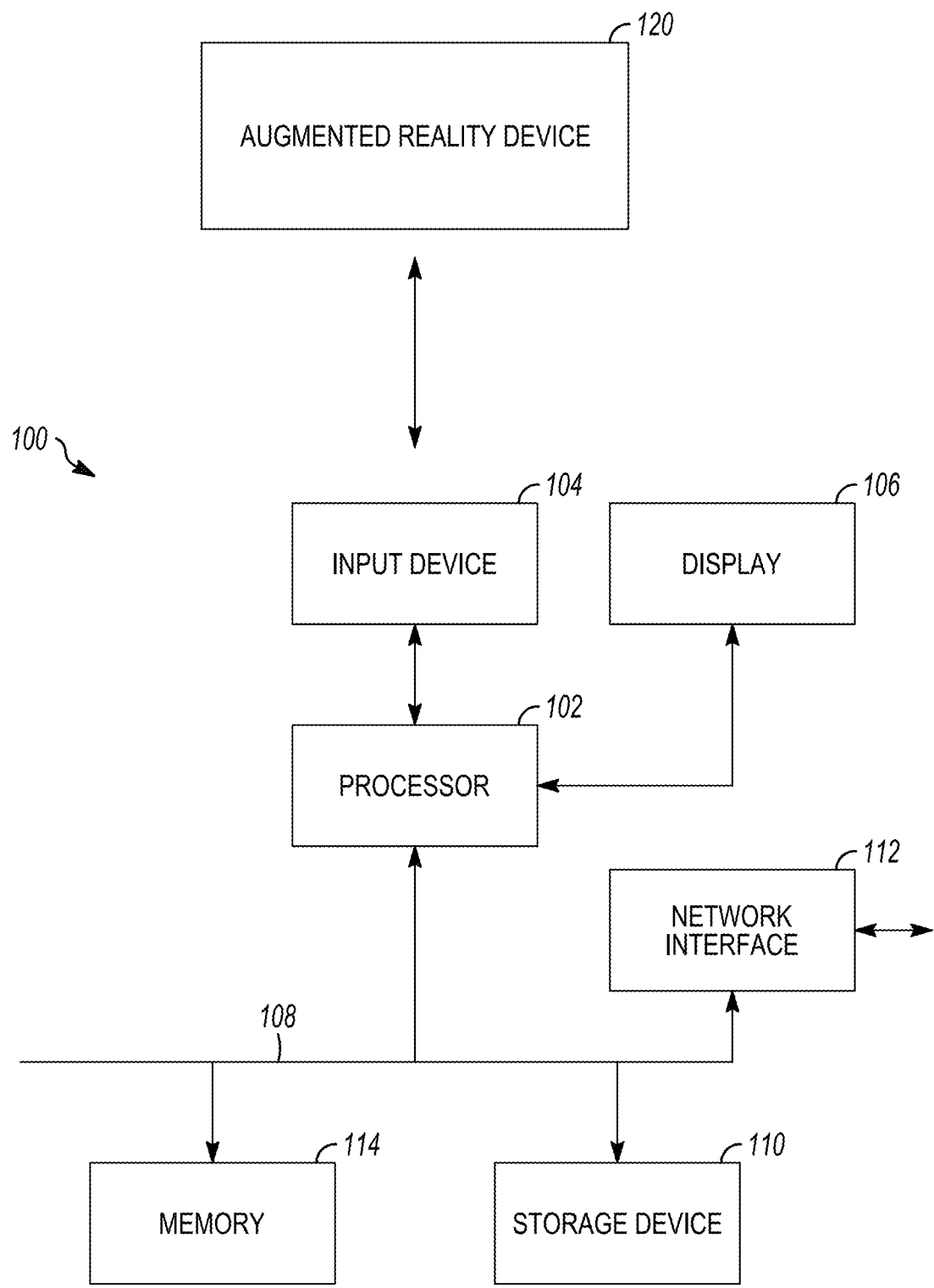
FIG. 1 generally illustrates a computing device according to the principles of the present disclosure.

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

As described, pharmacists and pharmacy technicians typically receive requests to fulfill pharmacy orders that include various pharmacy items. The pharmacy items may include medicine, medicine accessories, or other suitable items. In order to fulfill the pharmacy order, pharmacy technician (e.g., or the pharmacist) retrieves the items of a pharmacy order from a stockroom and brings the items to a workstation where the pharmacy technician fulfills the pharmacy order. Such stockrooms may be relatively large and may include a plurality or shelves for storing various pharmacy items. Pharmacists and/or pharmacy technicians may have to traverse multiple rows of shelves or access multiple rooms, which may be a significant distance, in order to retrieve all required items for the pharmacy order, which may be difficult and time consuming.

Additionally, items in the stockroom are typically stored in bulk quality. Accordingly, when the pharmacy technician retrieves the items from the stockroom, the pharmacy technician typically determines a quantity for each of the items required to fulfill the pharmacy order. In addition, after the pharmacy technician prepares the items for the pharmacy order, the items in the pharmacy order are typically verified, usually by a pharmacist. Such manual retrieval of stock items, inventory management, and verification can be cost and resource intensive and may be prone to human error.

Accordingly, systems and methods, such as those described herein, that are configured to improve pharmacy order fulfillment by providing pharmacy order fulfilment automation and guided access to stockroom items, may be desirable. In some embodiments, the systems and methods described herein may be configured to use augmented reality in order to fulfill a pharmacy order. The pharmacy order may be an order from a pharmacy customer and may include pharmacy items, such as medicine (e.g., prescription or non-prescription), pharmacy accessories (e.g., pads, syringes, measuring devices, and the like), other items, or a combination thereof.

The systems and methods described herein may be configured to use image-capturing capabilities of an augmented reality device to capture video data that includes a plurality of images of at least a portion of a pharmacy workstation. The systems and methods described herein may be configured to read or analyze the plurality of images of the video data to identify objects of interest in the video data. The objects of interest may include pharmacy items, such as medicine, pharmacy accessories, and the like.

In some embodiments, the systems and methods described herein may be configured to use a trained machine learning network (e.g., a trained convolutional neural network) in communication with the augmented reality device to classify the detected objects of interest. In some embodiments, the systems and methods described herein may be configured to identify or read barcodes on at least some of the objects using the model derived from the machine learning network (e.g., the convolutional neural network) to classify the detected objects.

In some embodiments, the systems and methods described herein may be configured to update a workstation inventory list based on the classification of the detected objects of interest. In some embodiments, the systems and methods described herein may be configured to identify a boundary defining an opening of a container in the video data. In some embodiments, systems and methods described herein are configured to detect the boundary defining the opening of the container using color filtering. In some embodiments, systems and methods described herein are configured to detect the boundary defining the opening of the container using edge detection. The edge detection may include Canny edge detection or other suitable edge detection. In some embodiments, systems and methods described herein are configured to detect the boundary defining the opening of the container using line detection. The line detection may include Hough transform line detection or other suitable line detection. Hough transformation line detection may include a feature extraction technique that uses a two-dimensional array (e.g., referred to as an accumulator) to detect lines in images.

In some embodiments, the container may include a box, shipping container, or other suitable container configured to enclose the pharmacy items of a pharmacy order. The container may include an opening, the boundary of which may be identified using the systems and methods described herein. For example, the container may be an open top polymer container, at which the systems and methods described herein may be configured to can define the boundary (e.g., a virtual boundary) of the open top. In some embodiments, the systems and methods described herein may be configured to update an objects in container list based on a determination that at least one of the classified objects passed the boundary, which may include the virtual boundary defined by the systems and methods described herein. The systems and methods described herein may be configured to generate information corresponding to the pharmacy order based on, at least, the objects in container list. In some embodiments, the systems and methods described herein may be configured to display, using a display device, the information.

In some embodiments, the systems and methods described herein may be configured to update the workstation inventory list based on the determination that at least one of the classified objects passed the boundary. In some embodiments, the systems and methods described herein may be configured to provide, to the augmented reality device or a display of a computing device, an indication corresponding to the objects in container list. In some embodiments, the systems and methods described herein may be configured to determine whether the objects in container list is the same as an expected objects list. In some embodiments, the systems and methods described herein may be configured to display, on a display device, that the pharmacy order is fulfilled based on a determination that objects in container list is the same as the expected objects list.

In some embodiments, the systems and methods described herein may be configured to use a display of the augmented reality device to provide guided access to a user (e.g., a pharmacist and/or pharmacy technician) to a stockroom. For example, the augmented reality device may include a display system (e.g., eyeglasses or goggles) worn by the user. The display system may include a hands-free display. The systems and methods described herein may provide a map and/or navigation instructions to the user by overlaying the map, the navigation instructions, and/or other information on lenses of the display system, such that the user perceives the map, navigation instructions, and/or other information while looking through the lenses at the real world (e.g., walkway, stockroom, and the like). The map, navigation instructions, and/or other information may guide the user through the real world to stock items required for fulfilling the pharmacy order.

In some embodiments, the systems and methods described herein may be configured to train a trainable network (e.g., a convolutional neural network) to recognize various objects, such as pharmacy items, a pharmacy workstation, containers associated with the pharmacy order, other suitable objects, or a combination thereof.

FIG. 1 generally illustrates a detailed view of a computing device 100 according to the principles of the present disclosure. The computing device 100 may be configured to train a network (e.g., a convolutional neural network) to recognize objects (e.g., such as those described), to provide automation to pharmacy order fulfilment, and to provide guides access to various pharmacy items in respective stockrooms or other suitable locations. The computing device 100 may be any suitable computing device, such as a mobile computing device, a laptop computing device, a desktop computing device, a server-computing device, or any other suitable computing device.

The computing device 100 may include a processor 102 configured to control the overall operation of computing device 100. The processor 102 may include any suitable processor, such as those described herein, which may be configured to load specific instructions and operate as a dedicated device. The computing device 100 may also include a user input device 104 that is configured to receive input from a user of the computing device 100 and to communicate signals representing the input received from the user to the processor 102. For example, the user input device 104 may include a button, keypad, dial, touch screen, audio input interface, visual/image capture input interface, input in the form of sensor data, etc.

In some embodiments, the input device 104 may include or be in communication with an augmented reality device 120. The augmented reality (AR) device 120 may include any suitable augmented reality device configured to provide input, such as image data or other suitable input, to the input device 104. In some embodiments, the augmented reality device 120 includes a wearable augmented reality device, such as eyeglasses, goggles, or other suitable wearable augmented reality device. The wearable augmented reality device may include a transparent screen that allows a user to see through the screen and allows images to be displayed on the screen. The AR device 120 may include an input mechanism, such as an image-capturing device (e.g., a camera or other suitable image-capturing device), an audio-capturing device (e.g., a microphone or other suitable audio-capturing device), one or more suitable sensors (e.g., global position system sensors, gyroscopic sensor, accelerometer, other suitable sensors, or a combination thereof), other suitable input mechanism, or a combination thereof.

The computing device 100 may include a display 106 that may be controlled by the processor 102 to display information to the user. A data bus 108 may be configured to facilitate data transfer between, at least, a storage device 110 and the processor 102. The computing device 100 may also include a network interface 112 configured to couple or connect the computing device 100 to various other computing devices or network devices via a network connection, such as a wired or wireless connection. In some embodiments, the network interface 112 includes a wireless transceiver.

The storage device 110 may comprise a single disk or a plurality of disks (e.g., hard drives), and includes a storage management module that manages one or more partitions within the storage device 110. In some embodiments, storage device 110 may include flash memory, semiconductor (solid state) memory or the like. The computing device 100 may also include a memory 114. The memory 114 may include Random Access Memory (RAM), a Read-Only Memory (ROM), or a combination thereof. The memory 114 may store programs, utilities, or processes to be executed in by the processor 102. The memory 114 may provide volatile data storage, and stores instructions related to the operation of the computing device 100.

Figure 2:
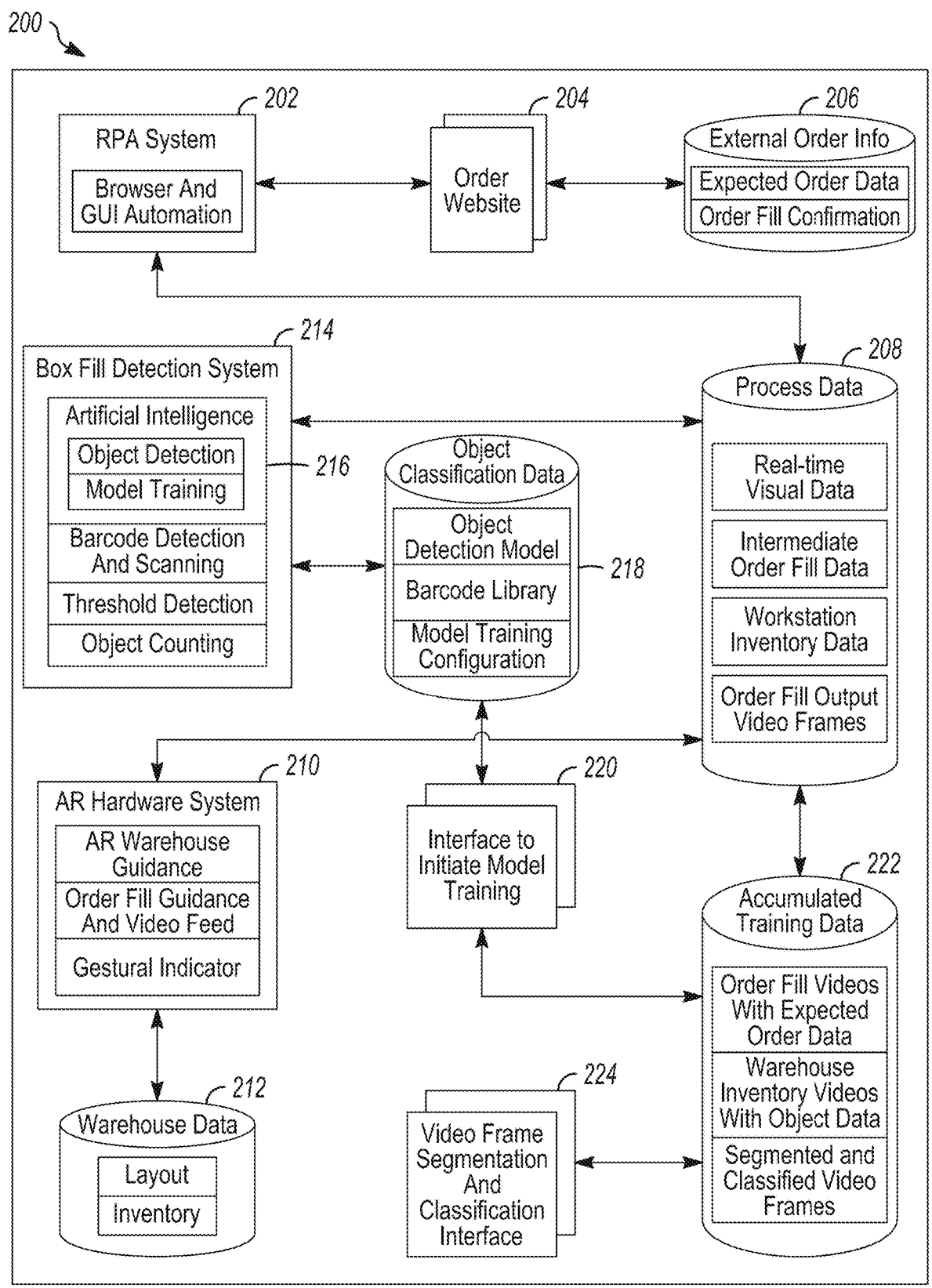
FIG. 2 generally illustrates a loose pharmacy item detection system according to the principles of the present disclosure.

FIG. 2 generally illustrates a loose pharmacy item detection system 200 according to the principles of the present disclosure. The system 200 may be partially embodied in the computing device 100 or in another computing device or plurality of computing devices (e.g., such as a server farm or cloud-based computing system) in communication with the computing device 100. For example, the processor 102 may executed instructions stored in the memory 114 to perform at least some of the functions of the system 200. In some embodiments, a portion of the system 200 may disposed on the AR device 120. For example, the AR device 120 may include a corresponding processor that executes instructions stored in a corresponding memory to perform at least some of the functions of the system 200.

The system 200 includes a robotic process automation (RPA) system 202. The RPA system 202 may be configured to interface and/or communicate with an order website 204 to receive pharmacy orders. For example, a pharmacy customer may access a customer interface disposed on the order website 204 or other suitable location. The customer may provide the customer interface with external order information 206. The external order information 206 may include prescription information indicating a type and amount of medicine and/or accessories. Additionally, or alternatively, the external order information 206 may include instructions indicating special conditions for the pharmacy order, such as storage temperatures of certain medicine, and other suitable information. The RPA system 202 may receive a notification from the order website 204 indicating a pharmacy order. Additionally, or alternatively, the RPA system 202 may access the order website 204 to determine whether a pharmacy order is available.

The RPA system 202 may communicate the pharmacy order and any corresponding information to process data 208. The RPA system 202 may store the data as intermediate order fill data and/or other suitable data. The process data 208 may include data or other information stored in a storage medium. For example, the process data 208 may be stored in the storage device 110 of the computing device 100. In some embodiments, the process data 208 may be organized as a database or multiple databases.

The system 200 includes an augmented reality (AR) hardware system 210. The AR hardware system 210 may be disposed on the computing device 100 and/or on the AR device 120. For example, the AR device 120 may include a wearable device, such as goggles, or other suitable wearable device. Output from the AR hardware system 210 may be provided by the AR device 120 and processing of the AR hardware system 210 may be disposed on the computing device 100. For example, the computing device 100 may receive input from the AR device 120 and may process the input to generate output that is displayed on a portion of the AR device 120, such as on a lens or transparent display screen of the AR device 120. Alternatively, the AR hardware system 210 may be substantially disposed on the AR device 120.

In some embodiments, the AR hardware system 210 may be configured to provide guided access to the user of the AR device 120. Guided access may include providing an augmented reality interface in order to provide directions to various pharmacy items in a corresponding stockroom. The augmented reality interface may include a map or instructions displayed on the lens, the transparent display screen, or other display device of the AR device 120.

Figure 3:
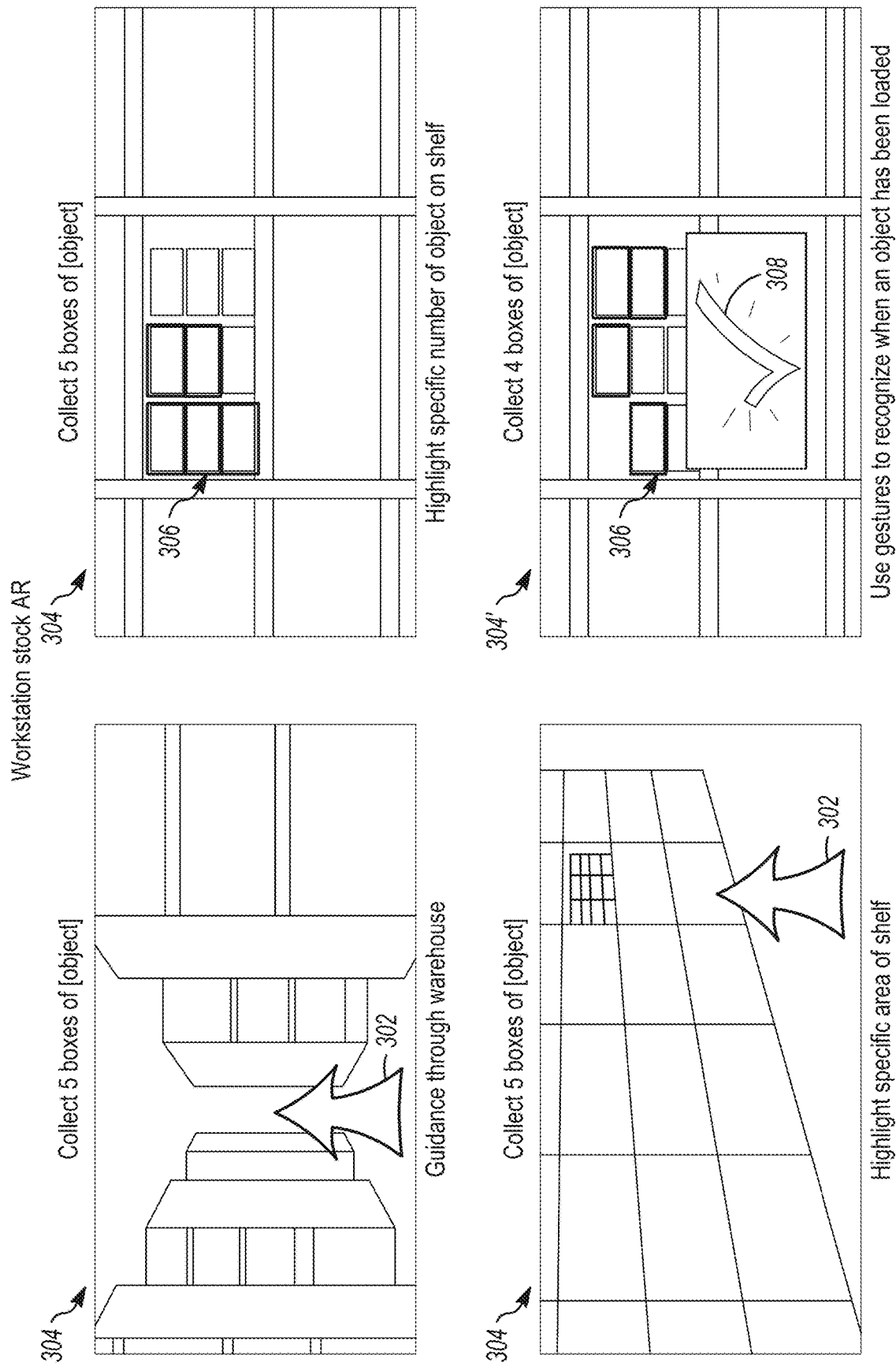
FIG. 3 generally illustrates a guided access output according to the principles of the present disclosure.

As is generally illustrated in FIG. 3, the guided access may include directional symbols 302. The directional symbols 302 may indicate a direction the user is to take in order to traverse a path to various pharmacy items associated with the pharmacy order or a location of one or more pharmacy items on a shelf or other suitable location within the stockroom. The guided access may include item information 304. The item information 304 may include a quantity of items that the user is to retrieve from the stockroom or other suitable information.

In some embodiments, the AR hardware system 210 may communicate with the process data 208 to retrieve data to generate the guided access. For example, the AR hardware system 210 may retrieve from the process data 208 intermediate order fill data, workstation inventory data, other suitable data, or a combination thereof. Additionally, or alternatively, the AR hardware system 210 may access warehouse data records 212 to retrieve stockroom layout data, inventory data, other suitable data, or a combination thereof.

The warehouse data records 212 may be disposed on a remotely located computing device or computing system, such as a cloud computing system, a server farm, other suitable computing devices or computing system, or a combination thereof. In some embodiments, the warehouse data records 212 may be disposed on the AR hardware system 210. For example, AR hardware system 210 may download the warehouse data records 212 from a remotely locating computing device or computing server or the AR hardware system 210 or the AR hardware system 210 may be preprogrammed with data from the warehouse data records 212.

In some embodiments, the AR hardware system 210 may generate data to be stored in the warehouse data records 212. For example, the AR hardware system 210 may capture images of the stockroom accessed by the user of the AR device 120. As described, the AR device 120 may include an image-capturing device, such as a camera or other suitable image-capturing device.

The image-capturing device may be configured to capture image data corresponding to an environment within a field of view of the AR device 120. The image data may include a plurality of images and/or video data comprising a plurality of images of the environment within the field of view of the AR device 120. The AR device 120 may include a neural network or may be in communication with a neural network remotely located from the AR device 120, such as a neural network on the computing device 100, a cloud computing device, a server in a server farm, or other suitable remotely located computing device. The neural network may include a convolutional neural network or other suitable neural network. As will be described, the neural network may be trained to recognize aspects of the stockroom and/or inventory items in the stockroom. The AR device 120 may provide the image data to the neural network. The neural network may identify aspects of the stockroom and/or inventory in the stockroom. The neural network may then classify the identified aspects of the stockroom and/or inventory in the stockroom in order to generate data for the warehouse data records 212.

The AR hardware system 210 may generate the directional symbols 302, the item information 304, other suitable symbols or information, or a combination thereof. As the user traverses the path to the inventory items required for the pharmacy order, the AR hardware system 210 may highlight inventory containers 306 on stockroom shelves or other suitable location in the stockroom. The user may then perform a gesture to indicate that an inventory container 306 has been retrieved. The gesture may include one or more motions to retrieve the inventory container 306, a specific gesture, such as a predetermined hand movement, or other suitable gesture.

In some embodiments, the AR hardware system 210 may be configured to recognize the gesture and may provide a visual acknowledgement 308 that the user has retrieved the inventory container 306. The visual acknowledgement 308 may include a symbol, such as a checkmark, an emoji, or other suitable visual acknowledgement. The AR hardware system 210 may display the visual acknowledgement 308, via one or more lenses of the AR device 120 or other suitable display. For example, the AR hardware system 210 may overlay the visual acknowledgement 308 on the received inventory container 306.

In some embodiments, the AR hardware system 210 is configured to update the item information 304 in response to the user retrieving the inventory container 306. For example, the AR hardware system 210 may determine a remaining item count based on the contents of the inventory container 306. The AR hardware system 210 may determine the contents of the inventory container 306 based on the inventory data stored in the warehouse data records 212. The inventory data may indicate a type of items in the inventory container 306, a count of the items in the inventory container 306, other suitable data, or a combination thereof. The AR hardware system 210 may decrement a value associated with the item information 304. For example, the AR hardware system 210 may generate item information 304 based on the intermediate order fill data of the process data 208, the inventory data of the warehouse data records 212, other suitable data, or a combination thereof.

In some embodiments, the system 200 may include a box fill detection system 214. The box fill detection system 214 may be disposed on the computing device 100. In some embodiments, the box fill detection system 214 may be disposed on the AR device 120, the computing device 100, a remotely located computing device, or a combination thereof. The box fill detection system 214 includes an artificial intelligence 216 that may include a neural network, such as a convolutional neural network or other suitable neural network, a machine learning system, a computer vision system, a deep learning system, other artificial intelligence systems, or a combination thereof. For example, the artificial intelligence 216 may include or communicate with the convolutional neural network described with respect to the AR hardware system 210.

The neural network of the artificial intelligence 216 may include, for example, a deep learning network that typically includes various layers that process inputs, such as the image data generated by the AR device 120, and generate outputs (e.g., class scores, image classifications, or other suitable output). For example, the neural network can include convolution layers that process sets of inputs with convolution kernels to generate sets of outputs. Convolutional layers are typically configured to detect high-level features of the inputs, such as edged, curves, simple colors, and the like.

The output of the convolutional layers may be provided to a fully connected layer. The fully connected layer typically connects every neuron in one layer of the neural network to every other neuron in another layer of the neural network. The fully connected layer is configured to receive inputs from the convolutional layers and generate outputs that can be used to predict classifications for images associated with the inputs. For example, during training of the neural network, as will be described, a plurality of images may be provided to the neural network (e.g., using the convolutional layers, as described). The neural network may learn by using the fully connected layer to classify each of the images.

Figure 4:
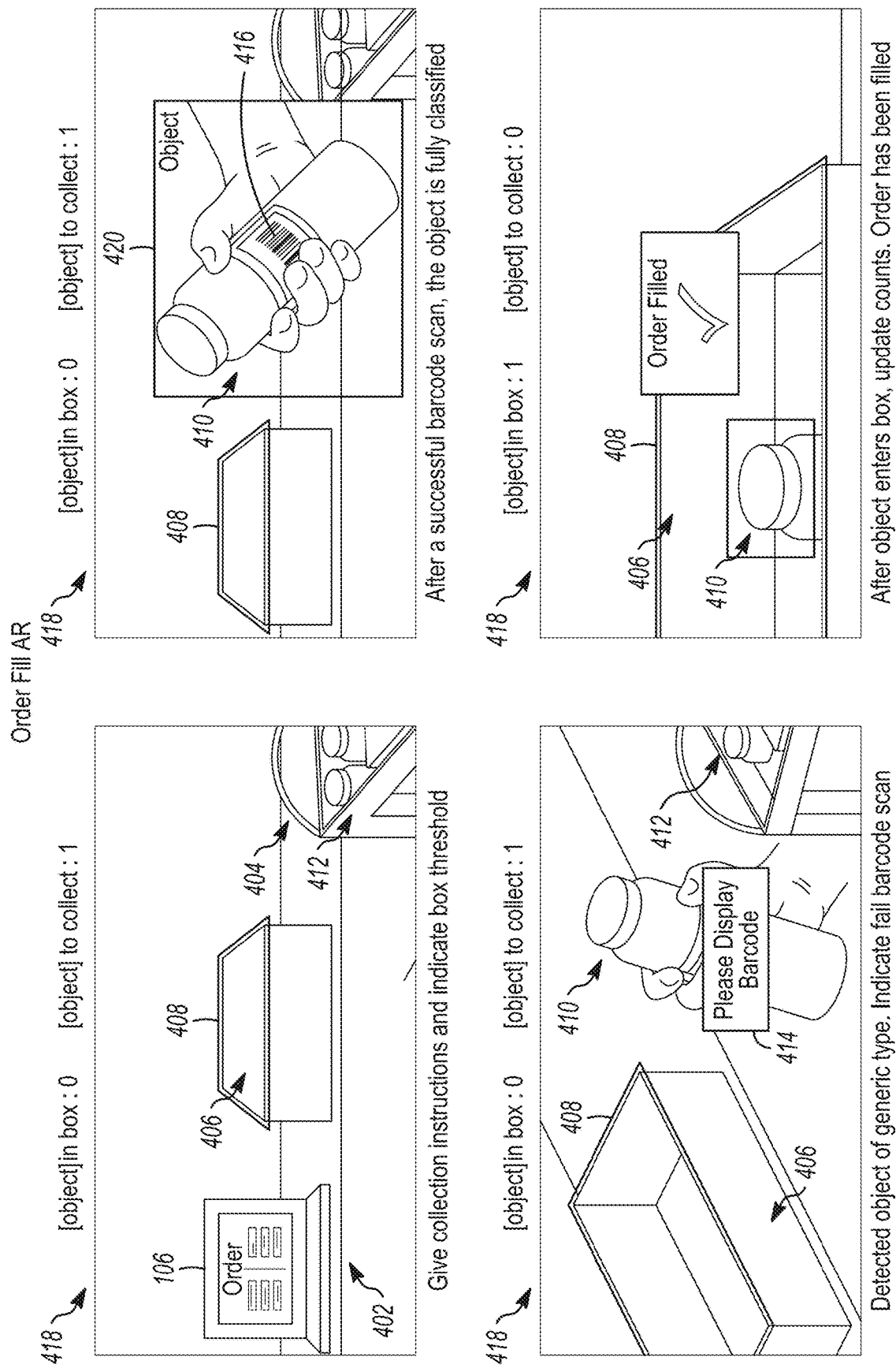
FIG. 4 generally illustrates an order fill output according to the principles of the present disclosure.

The box fill detection system 214 may use the artificial intelligence 216 to identify objects on a workstation 402 as is generally illustrated in FIG. 4. The box fill detection system 214 reads image frames of the image data generated by the AR device 120. The box fill detection system 214 may retrieve the image frames from accumulated training data 222. The accumulated training data 222 may communicate with a video frame segmentation and classification interface 224. The video frame segmentation and classification interface 224 may receive the image data from the AR device 120. The video frame segmentation and classification interface 224 may segment and classify the image frames of the image data. The accumulated training data 222 may store segmented and classified image frames.

The box fill detection system 214, using the artificial intelligence 216, may load an object detection model. The object detection model may include a model generated during training of the artificial intelligence 216. The box fill detection system 214 may retrieve the model from the object classification data 218. The artificial intelligence 216 reads a first image frame of the image data and identifies objects in the first image frame. The box fill detection system 214, using the artificial intelligence 216, identifies the workstation 402 in the first image frame.

The box fill detection system 214, using the artificial intelligence 216, may identify various objects on the workstation 402 by reading the first image frame and/or one or more other image frames of the image data. For example, the box fill detection system 214 may identify a surface 404 and a display, such as the display 106 of the computing device 100, or other suitable display on the workstation 402. In some embodiments, the computing device 100 may output, via the display 106, pharmacy order information corresponding to the pharmacy order. The computing device 100 may access the intermediate order fill data of the process data 208. The computing device 100 generates the pharmacy order information using the intermediate order fill data.

The box fill detection system 214, using the artificial intelligence 216, may identify a container 406 on the workstation 402. The user filling the pharmacy order may package the pharmacy order in the container 406. The container 406 may include a box, a prescription bottle, a bag, or any other suitable container.

The box fill detection system 214 may be configured to use the artificial intelligence 216 to identify a threshold 408 of the container 406. The threshold 408 may include an edge or lip of the container 406. In some embodiments, the threshold 408 may define a plane perpendicular the container 406. Additionally, or alternatively, the threshold 408 may define a boundary between items outside of the container 406 and items in the container 406.

In some embodiments, the box fill detection system 214 may be configure to identify items retrieved by the user filling the pharmacy order from a workstation inventory 412. For example, the user may retrieve a pharmacy item 410 required for the pharmacy order from the workstation inventory 412. The box fill detection system 214, using the artificial intelligence 216, identify the item 410 using information on the item 410. For example, the box fill detection system 214 may be configured to read a bar code on the item 410, a label on the item 410, a description on the item 410, other suitable information on the item 410 or a combination thereof. The box fill detection system 214 may read an image frame of the image data captured by the AR device 120.

The box fill detection system 214, using the artificial intelligence 216, may first identify a general type of or class of item of the item 410 by analyzing characteristics of the item 410, such as shape, color, size, other suitable characteristics, or a combination thereof. For example, the box fill detection system 214 may determine that the item 410 is a container of medicine based on the shape, color, size, or a combination thereof of the item 410. The shape and size of the item may be defined without regard to the orientation of the item such that the item may be identified based on any orientation thereof. The box fill detection system 214 may then determine a specific type or class of the item 410 using information 416 on the item 410.

For example, the box fill detection system 214 may attempt to identify the item 410 by reading an identification mark on the item 410 (e.g., a barcode, an OR code, a two-dimensional (2D) data matrix symbol, an alphanumerical identifier, or the like). For ease of description, the present specification may refer to bar codes for any of these unique identifiers. If the box fill detection system 214 is unable to read or analyze the information on the item 410 (e.g., because the information is blocked or not facing the AR device 120), the box fill detection system 214 may generate output to be provided to the AR device 120. The output may include an indication, such as the indication 414, instructing the user of the AR device 120 to display information 416 on the item 410 (e.g., by moving the item 410, such that the information is captured by the AR device 120). The box fill detection system 214 may generate a barcode reader box 420 (e.g., within a bounding box of the item 410, as will be described).

The box fill detection system 214 may overlay the barcode reader box 420 onto the image frame and/or one or more lenses of the AR device 120. The box fill detection system 214 may continue to read or analyze the item 410 in the barcode reader box 420 until the box fill detection system 214 is able to read the information 416 and identify the specific type or class of the item 410. The box fill detection system 214 may compare the information 418 to barcodes stored in the object classification data 218 or the box fill detection system 214 may use a barcode decoder mechanism to read the barcode. The box fill detection system 214 determines the specific type of class of the item 410 based on the information 416 and a corresponding barcode on the object classification data 218. It should be understood that while only a barcode is described herein, the box fill detection system 214 may use any suitable information to identify the specific type or class of the item 410.

The user may then place the item 410 in the container 406. The box fill detection system 214 may determine whether the item 410 has passed the threshold 408 of the container 406. When the box fill detection system 214 determines that the item 410 has passed the threshold 408 of the container 406, the box fill detection system 214 determines that item 410 has been placed in the container 406.

In some embodiments, the box fill detection system 214 may display, via the AR device 120, order fill information 418. The order fill information 418 may include a count of items in the container 406, a count of items required to fill the pharmacy order, other suitable information, or a combination thereof. The box fill detection system 214 may update the order information in response to determining that an item, such as the item 410, has been placed in the container 406. For example, the box fill detection system 214 may decrement a count of items required to fill the pharmacy order and increment a count of items in the container 406. In some embodiments, the box fill detection system 214 may generate output indicating that the pharmacy order is complete in response to the count of items required to fill the pharmacy order equals 0. The box fill detection system 214 may provide the output to the AR device 120.

In some embodiments, the accumulated training data 222 may also include order fill videos with expected order data, warehouse inventory videos with object data, other suitable data, or a combination thereof. The data stored in the accumulated training data 222 may be used to identify objects in the image data, as described. Additionally, or alternatively, the data in accumulated training data 222 may be used train or continue to train the system 200. For example, an interface to initiate model training 220 may be used by the box fill detection system 214, the AR hardware system 210, and/or any other suitable system to initiate training using the data in the accumulated training data 222.

In some embodiments, the computing device 100, the AR device 120, the system 200, or a combination thereof may perform the methods described herein. However, the methods described herein as performed by the computing device 100, the AR device 120, the system 200, or a combination thereof are not meant to be limiting, and any type of software executed on a computing device or a combination of various computing devices can perform the methods described herein without departing from the scope of this disclosure.

Figure 5:
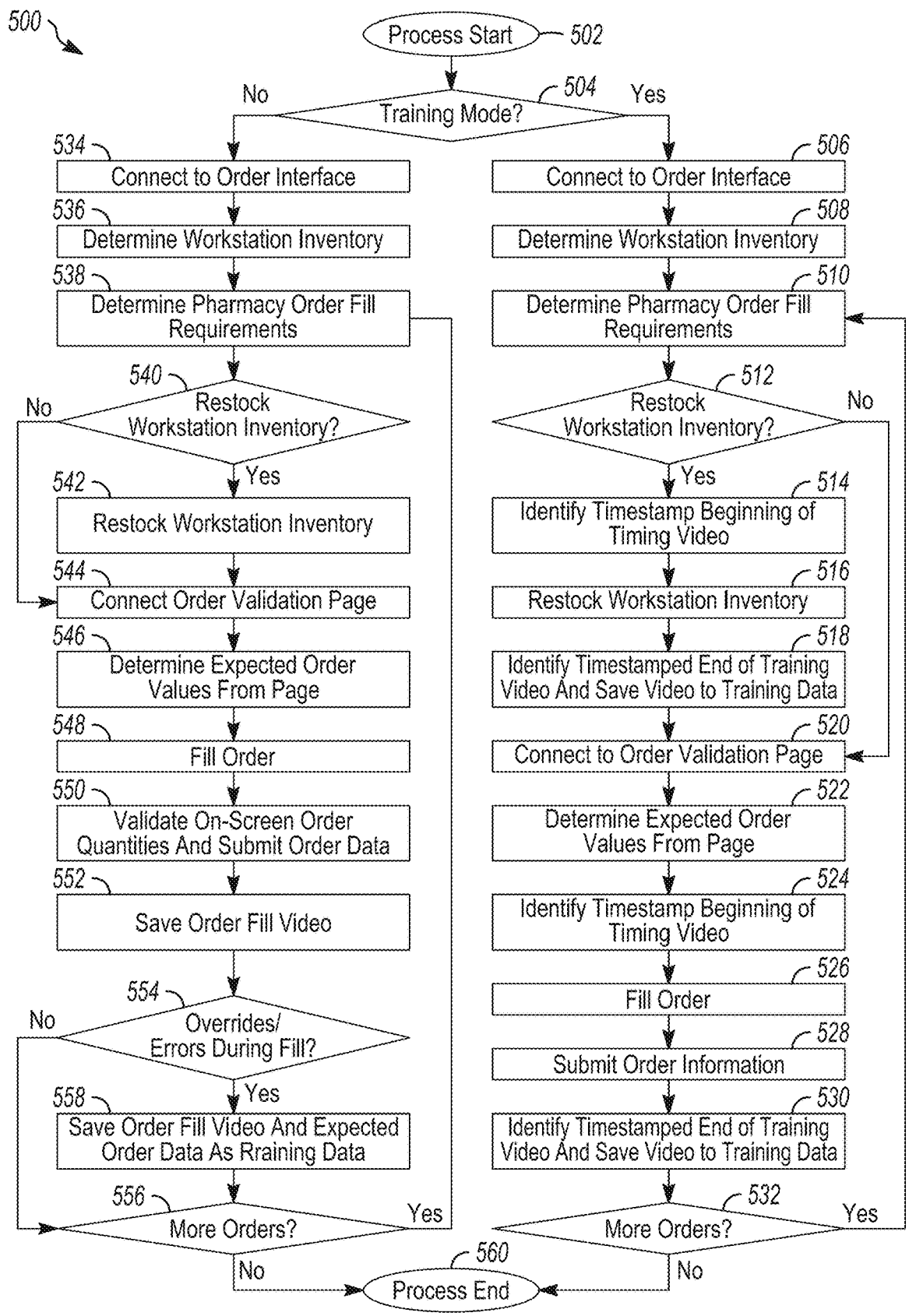
FIG. 5 is a flow diagram generally illustrating a pharmacy order fill method according to the principles of the present disclosure.

FIG. 5 is a flow diagram generally illustrating a pharmacy order fill method 500 according to the principles of the present disclosure. At 502, the method 500 begins. At 504, the method 500 determines whether to enter a training mode. For example, the computing device 100 may receive input from a user or programmer of the computing device 100. The input may indicate instructions to enter into a training mode or instructions to enter into a non-training mode, such as a production mode, use mode, object detection mode, or other suitable mode of operation. If the computing device 100 determines that the input indicates instructions to enter into a training mode, the method 500 continues at 506. If the computing device 100 determines that the input does not indicate instructions to enter into a training mode, the method 500 continues at 534.

At 506, the method 500 connects to an order interface. For example, the RPA system 202 may connect to order website 204 or other suitable interface to obtain order information for a pharmacy order. At 508, the method 500 determines current workstation inventory. For example, the box fill detection system 214 may access workstation inventory data stored in the process data 208. Additionally, or alternatively, the current workstation inventory may be manually supplied by the user. The box fill detection system 214 may determine a current workstation inventory of the workstation 402 based on the workstation inventory data.

In some embodiments, the box fill detection system 214 may use the artificial intelligence 216 to determine a current workstation inventory. For example, the box fill detection system 214 may access or receive image data from the AR device 120. The box fill detection system 214, using the artificial intelligence 216, may analyze the image data, as described, to identify objects in image frames of the image data. The box fill detection system 214, using the artificial intelligence 216, may determine whether objects detected in the image frames are workstation inventory items or other items on or near the workstation 402 based on the classification of the objects detected in the image frames. The box fill detection system 214 may update the workstation inventory data stored in the process data 208 based on the detected workstation inventory items.

In some embodiments, the box fill detection system 214 may identify inventory retrieved from the warehouse. The box fill detection system 214 may increment a count associated with items on a workstation inventory list based on the retrieved inventory. For example, the box fill detection system 214 may identify a first item retrieved from the warehouse. The box fill detection system 214 determines whether the first item is on the workstation inventory list. If the box fill detection system 214 determines the first item is on the workstation inventory list, the box fill detection stem 214 increments the number of first items on the workstation inventory list by the number of first items retrieved form the warehouse. If the box fill detection system 214 determines that the first item is not on the workstation inventory list, the box fill detection system 214 creates an entry on the workstation inventory list corresponding to the first item and indicates the number of first items retrieved from the warehouse.

In some embodiments, the box fill detection system 214 may be configured to update the workstation inventory list in response to inventory items being placed in the container 406 or taken out of the container 406. For example, the box fill detection system 214 may decrement a count associated with an item on the workstation inventory list in response to the box fill detection system 214 determining that the item passed the container threshold 408 and was placed in the container 406. Conversely, the box fill detection system 214 may increment a count associated with an item on the workstation inventory list in response to the box fill detection system 214 determining that the item passed the container threshold 408 and was removed from the container 406.

At 510, the method 500 determines pharmacy order fill requirements. For example, box fill detection system 214 may access intermediate order fill data stored on the process data 208 in order to determine pharmacy order fill requirements. The pharmacy order fill requirements may include a type and quantity (e.g. or amount) of medicine, a type and quantity (e.g., or amount) of accessories, pharmacy user information (e.g., data of birth, insurance information, delivery information, other suitable information or a combination thereof), special instructions, other suitable requirements, or a combination thereof.

At 512, the method 500 determines whether to restock the workstation inventory. For example, the box fill detection system 214 may comparing the determined workstation inventory with the pharmacy order fill requirements. If the box fill detection system 214 determines that the workstation inventory includes all items in the pharmacy order fill requirements, the method 500 continues at 520. If the box fill detection system 214 determines that the workstation inventory does not include all of the items in the pharmacy order fill requirements of if the box fill detection system 214 determines that the workstation inventory is below a threshold of inventory items, the method 500 continues at 514.

At 514, the method 500 identifies a timestamp at the beginning of a training video. For example, the box fill detection system 214 may communicate with the AR device 120. The box fill detection system 214 may selectively instruct the AR device 120 to begin capturing data, such as video data comprising a plurality of images, while the workstation inventory is being restocked. The AR device 120 may begin capturing video. The box fill detection system 214 may overlay or insert a timestamp at the beginning of the training video to indicate the start time of the training video. At 516, the method 500 restocks the workstation. For example, the user of the AR device 120 may retrieve items from the stockroom, as described. The AR device 120 captures the image data while the user of the AR device 120 retrieves the items from the stockroom and restocks the workstation 402. The box fill detection system 214, using the artificial intelligence 216, may determine, based on image data of the workstation 402, that the workstation inventory is restocked. At 518, the method 500 identifies a timestamp at the end of the training video and stores the training video. For example, the box fill detection system 214 instructs the AR device 120 to stop capturing image data. The box fill detection system 214 overlays or inserts a timestamp at the end of the training video to indicate the end time of the training video. The box fill detection system 214 stores the training video in the accumulated training data 222.

At 520, the method 500 connects to an order validation page. For example, RPA system 202 may connect to the order website 204. At 522, the method 500 determines expected order values from the validation page. For example, the RPA system 202 may retrieve expected order data from the external order information 206 via the order website 204.

At 524, the method 500 identifies a timestamp at the beginning of a training video. For example, the box fill detection system 214 may communicate with the AR device 120. The box fill detection system 214 may selectively instruct the AR device 120 to begin capturing data, such as video data comprising a plurality of images, while the order is being filled by the user of the AR device 120. The AR device 120 may begin capturing video. The box fill detection system 214 may overlay or insert a timestamp at the beginning of the training video to indicate the start time of the training video. At 526, the method 500 fills the order. For example, the user of the AR device 120 may fill the pharmacy order, as described. The AR device 120 captures the image data while the user of the AR device 120 places items in the container 406. The box fill detection system 214, using the artificial intelligence 216, may determine, based on image data of the workstation 402 and the identified container threshold 408, that the container 406 includes all required items of the pharmacy order.

At 528, the method 500 submits order information. For example, the box fill detection system 214 may generate order information. The order information may indicate that the pharmacy order is filled. Additionally, or alternatively, the order information may indicate shipping and/or tracking information of the pharmacy order. The box fill detection system 214 may communicate the order information to the process data 208. The RPA system 202 may retrieve the order information from the process data 208. The RPA system 202 may communicate the order information to the external order information 206 via the order website 204.

At 530, the method 500 identifies a timestamp at the end of the training video and saves the training video. For example, the box fill detection system 214 instructs the AR device 120 to stop capturing image data. The box fill detection system 214 overlays or inserts a timestamp at the end of the training video to indicate the end time of the training video. The box fill detection system 214 stores the training video in the accumulated training data 222. At 532, the method 500 determined whether there are other orders to fill. For example, the RPA system 202 may access the external order information 206 via the order website 204 to determine whether there are other pharmacy orders to fill. If RPA system 202 determines that they are other pharmacy orders to fill, the method 500 continues at 510. If the RPA system 202 determines that there are no pharmacy orders to fill, the method 500 ends at 560.

At 534, the method 500 connects to an order interface. For example, the RPA system 202 may connect to order website 204 or other suitable interface to obtain order information for a pharmacy order. At 536, the method 500 determines current workstation inventory. For example, the box fill detection system 214 may access workstation inventory data stored in the process data 208. The box fill detection system 214 may determine a current workstation inventory of the workstation 402 based on the workstation inventory data.

In some embodiments, the box fill detection system 214 may use the artificial intelligence 216 to determine a current workstation inventory. For example, the box fill detection system 214 may access or receive image data from the AR device 120. The box fill detection system 214, using the artificial intelligence 216, may analyze the image data, as described, to identify objects in image frames of the image data. The box fill detection system 214, using the artificial intelligence 216, may determine whether objects detected in the image frames are workstation inventory items or other items on or near the workstation 402 based on the classification of the objects detected in the image frames. The box fill detection system 214 may update the workstation inventory data stored in the process data 208 based on the detected workstation inventory items.

In some embodiments, the box fill detection system 214 may identify inventory retrieved from the warehouse. The box fill detection system 214 may increment a count associated with items on a workstation inventory list based on the retrieved inventory. For example, the box fill detection system 214 may identify a first item retrieved from the warehouse. The box fill detection system 214 determines whether the first item is on the workstation inventory list. If the box fill detection system 214 determines the first item is on the workstation inventory list, the box fill detection stem 214 increments the number of first items on the workstation inventory list by the number of first items retrieved form the warehouse. If the box fill detection system 214 determines that the first item is not on the workstation inventory list, the box fill detection system 214 creates an entry on the workstation inventory list corresponding to the first item and indicates the number of first items retrieved from the warehouse.

In some embodiments, the box fill detection system 214 may be configured to update the workstation inventory list in response to inventory items being placed in the container 406 or taken out of the container 406. For example, the box fill detection system 214 may decrement a count associated with an item on the workstation inventory list in response to the box fill detection system 214 determining that the item passed the container threshold 408 and was placed in the container 406. Conversely, the box fill detection system 214 may increment a count associated with an item on the workstation inventory list in response to the box fill detection system 214 determining that the item passed the container threshold 408 and was removed from the container 406.

At 538, the method 500 determines pharmacy order fill requirements. For example, box fill detection system 214 may access intermediate order fill data stored on the process data 208 in order to determine pharmacy order fill requirements. The pharmacy order fill requirements may include a type and quantity (e.g. or amount) of medicine, a type and quantity (e.g., or amount) of accessories, pharmacy user information (e.g., data of birth, insurance information, delivery information, other suitable information or a combination thereof), special instructions, other suitable requirements, or a combination thereof. At 540, the method 500 determines whether to restock the workstation inventory. For example, the box fill detection system 214 may comparing the determined workstation inventory with the pharmacy order fill requirements. If the box fill detection system 214 determines that the workstation inventory includes all items in the pharmacy order fill requirements, the method 500 continues at 544. If the box fill detection system 214 determines that the workstation inventory does not include all of the items in the pharmacy order fill requirements of if the box fill detection system 214 determines that the workstation inventory is below a threshold of inventory items, the method 500 continues at 542.

At 542, the method 500 restocks the workstation. For example, the user of the AR device 120 may retrieve items from the stockroom, as described. The AR device 120 captures image data, such as video data comprising a plurality of images, while the user of the AR device 120 retrieves the items from the stockroom and restocks the workstation 402. The box fill detection system 214, using the artificial intelligence 216, may determine, based on image data of the workstation 402, that the workstation inventory is restocked.

At 544, the method 500 connects to the order validation page. For example, RPA system 202 may connect to the order website 204. At 546, the method 500 determines expected order values from the validation page. For example, the RPA system 202 may retrieve expected order data from the external order information 206 via the order website 204.

At 548, the method 500 fills the order. For example, the user of the AR device 120 may fill the pharmacy order, as described. The AR device 120 captures the image data while the user of the AR device 120 places items in the container 406. The box fill detection system 214, using the artificial intelligence 216, may determine, based on image data of the workstation 402 and the identified container threshold 408, that the container 406 includes all required items of the pharmacy order. At 550, the method 500 validates on-screen order qualities and submits order data. For example, the box fill detection system 214 may validate that information displayed on the AR device 120, the display 106, and/or the order website 204 is accurate. The box fill detection system 214 may compare expected quantities or values with the information displayed. The box fill detection system 214 may then generate the order information (e.g., or order data) and may communicate the order information, via the order website 204, to the external order information 206.

At 552, the method 500 saves the order fill video. For example, the box fill detection system 214 instructs the AR device 120 to stop capturing image data. The box fill detection system 214 stores the image data captured while the pharmacy order was filled in the process data 208. At 554, the method 500 determines whether overrides or errors occurring while filling the pharmacy order. The user of the AR device 120 may override an output, such as a decision, a detection, a classification, an indication, or other output of the box fill detection system 214. For example, the user of the AR device 120 may view information provided by the box fill detection system 214 on one or more lenses of the AR device 120. The information may indicate that, for example, the pharmacy order has been filled (e.g., all required items are in the container 406). The user of the AR device 120 may determine that the box fill detection system 214 mistakenly determined that the container 406 included all required items of the pharmacy order and may continue to fill the pharmacy order. The user of the AR device 120 may indicate the override, using any suitable input, to the box fill detection system 214.

If the box fill detection system 214 determines that no override or errors occurred, the method 500 continues at 556. If the box fill detection system 214 determines that at least one override or error occurred, then the method 500 continues at 558. At 556, the method 500 determined whether there are other orders to fill. For example, the RPA system 202 may access the external order information 206 via the order website 204 to determine whether there are other pharmacy orders to fill. If RPA system 202 determines that they are other pharmacy orders to fill, the method 500 continues at 538. If the RPA system 202 determines that there are no pharmacy orders to fill, the method 500 ends at 560. At 558, the method 500 saves the order fill video and expected order data as training data. For example, the box fill detection system 214 stores the image data and the expected order fill data in the accumulated training data 222.

Figure 6:
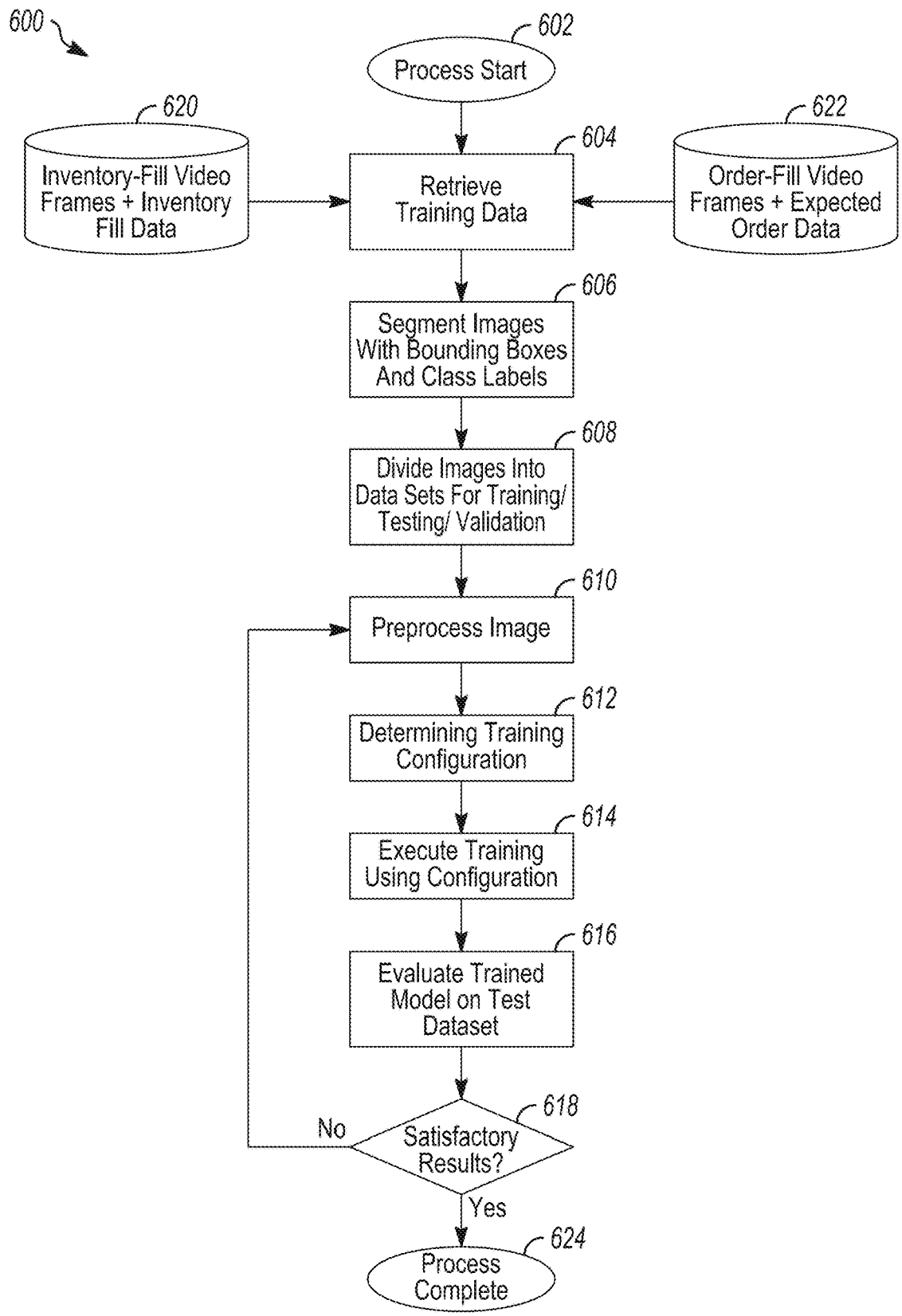
FIG. 6 is a flow diagram generally illustrating an initial object detection model training method according to the principles of the present disclosure.

FIG. 6 is a flow diagram generally illustrating an initial object detection model training method 600 according to the principles of the present disclosure. At 602, the method 600 begins. At 604, the method 600 retrieves training data. For example, the box fill detection system 214 may retrieve training data including inventory-fill video frames and inventory-fill data 620; and order-fill video frames and expected order data 622. The data 620 and the data 622 may be stored in the accumulated training data 222 or provided to the box detection system 214 by a programmer or user of the AR device 120 and/or the box fill detection system 214. The data 620 and 622 may include image data, such videos comprising a plurality of images.

At 606, the method 600 segments images with bounding boxes and class labels. For example, the programmer or user of the AR device 120 and/or the box fill detection system 214 may manually segment the plurality of images using bounding box information and class label information. The bounding box information may include a point, width, and height indicating the location of an object of interest in an image. For example, the bounding box information may include a box around the object of interest in the image. The class label information indicates the class of the object of interest. For example, the class label information may indicate that a general class of the object of interest is a container and/or the class label information may indicate that a specific class of the object of interest is a container for a particular type of medicine.

At 608, the method 600 divides the images into data sets for training, testing, and/or validation. For example, the programmer or user of the AR device 120 and/or the box fill detection system 214 may generate a training set of images comprising at least some of the images of the plurality of images. The training set of images may be provided, as will be described, to the artificial intelligence 216. The artificial intelligence 216 analyzes the objects of interest in the training set of images, including the bounding box information and the class label information for each of the corresponding images and stores information that the indicates how to detect similar objects of interest in other images. The artificial intelligence 216 may generate and store a model corresponding to training set of images.

The programmer or user of the AR device 120 and/or the box fill detection system 214 may generate a testing set of images comprising at least some of the images of the plurality of images. The testing set of images may be provided to the artificial intelligence 216. The artificial intelligence 216 may load a model corresponding to the testing set of images. The artificial intelligence 216 may use the model to identify objects of interest in the testing set of images.

The programmer or user of the AR device 120 and/or the box fill detection system 214 may generate a validation set of images comprising at least some of the images of the plurality of images. The validation set of images may be provided to the artificial intelligence 216. The models of the artificial intelligence 216 may be validated using the validation set of images.

At 610, the method 600 may preprocess the images. For example, the artificial intelligence 216 may preprocess the images provided to the artificial intelligence. The artificial intelligence 216 may be configured to preprocess the images by transforming the colors of the images, by changing the data structure of the images (e.g., from a jpg file type to a NumPy array), by changing dimensions of one or more of the images, by performing any other suitable preprocessing function, or a combination thereof. At 612, the method 600 determines a training configuration. For example, the artificial intelligence 216 may receive input from the programmer or user of the AR device 120 and/or the box fill detection system 214 indicating the training configuration.

At 614, the method 600 executes the training using the configuration. For example, the artificial intelligence 216 analyzes the objects of interest in the training set of images, including the bounding box information and the class label information for each of the corresponding images and stores a corresponding model that the indicates how to detect similar objects of interest in other images.

At 616, the method 600 evaluates the trained model on the test dataset. For example, the programmer or user of the AR device 120 and/or the box fill detection system 214 may provide the artificial intelligence 216 with the testing set of images. The artificial intelligence 216 may load a model corresponding to the testing set of images. The artificial intelligence 216 may use the model to identify objects of interest in the testing set of images. The artificial intelligence 216 outputs information indicating what the artificial intelligence 216 predicts the objects of interest in the testing set of images are.

The output may include bounding box information and class label information. The bounding box information may include a point, width, and height indicating the location of the objects of interest in the testing images. The class label information indicates the class of the object of interest. The class may be generic or specific. For example, the model may be trained to identify a generic class, such as a container, or a specific class, such as a container for a particular medicine. In some embodiments, the model may be trained to identify a generic class, such as a container and the box fill detection system 214 may be configured to read a barcode of the container, as described, to specifically classify the objects of interest.

At 618, the method 600 determines whether the results of the model test are satisfactory. For example, as described, the programmer or user of the AR device 120 and/or the box fill detection system 214 may use the validation set of images to validate the models of the artificial intelligence 216. Additionally, or alternatively, the programmer or user of the AR device 120 and/or the box fill detection system 214 may monitor a number of errors in the predictions provided by the artificial intelligence 216 during the test of the model.

If the results are satisfactory (e.g., the model validation was successful or the number of errors were below a threshold), the method 600 ends at 624. If the results are not satisfactory (e.g., the model validation was unsuccessful or the number of errors were above the threshold), the method 600 continues at 612. In some embodiments, the models generated by the artificial intelligence 216 may be trained and/or retrained using additional training sets, testing sets, and validation sets. The additional training sets, testing sets, and validation sets may be generated using any suitable images including but not limited to, the videos captured by the AR device 120 during a pharmacy order fulfillment and/or during a workstation restocking.

Figure 7:
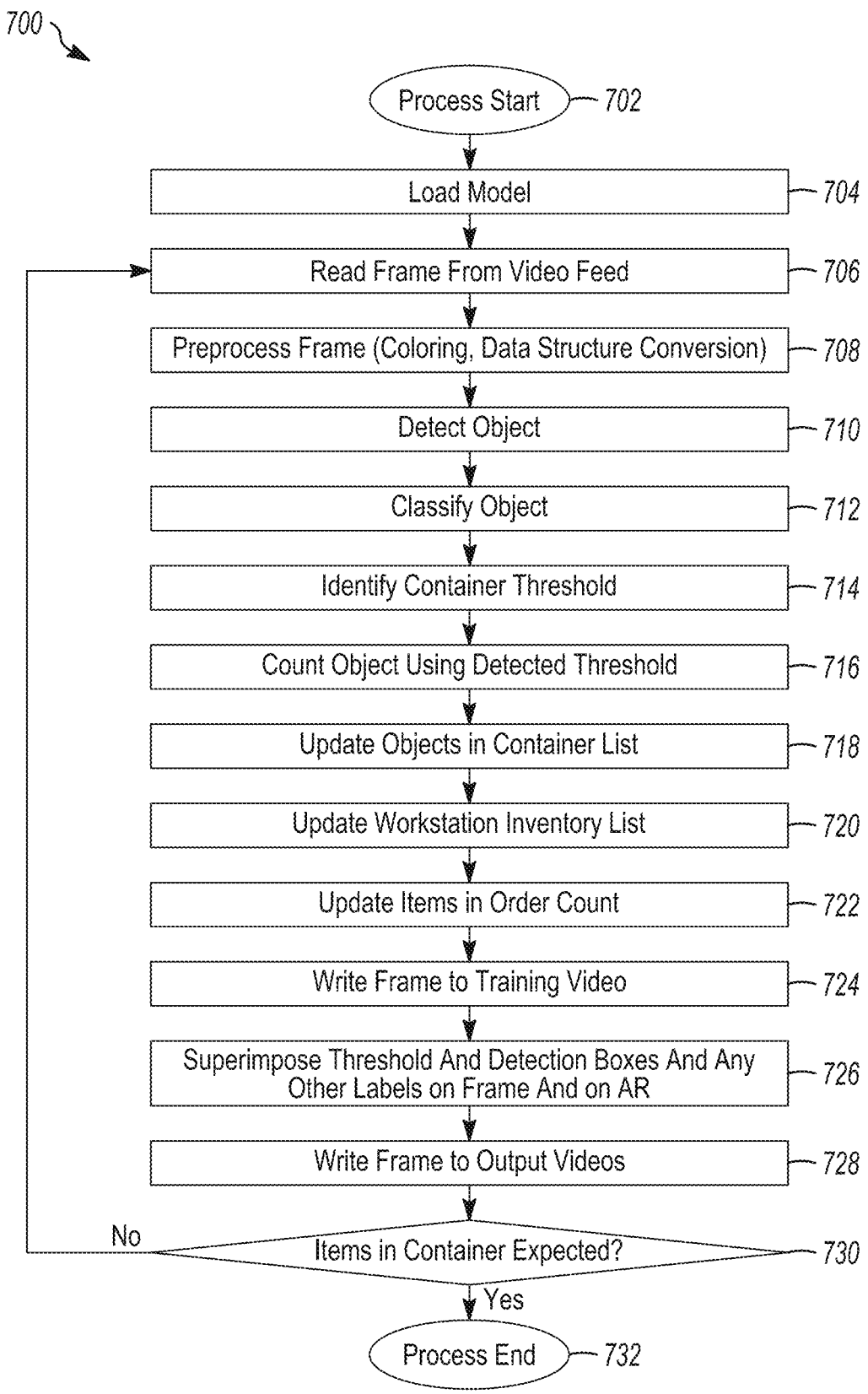
FIG. 7 is a flow diagram generally illustrating an object detection method according to the principles of the present disclosure.

FIG. 7 is a flow diagram generally illustrating an object detection method 700 according to the principles of the present disclosure. At 702, the method 700 begins. At 704, the method 700 loads a model. For example, the artificial intelligence 216 loads a model trained to detected pharmacy items. At 706, the method 700 reads a frame from a video feed. For example, the artificial intelligence 216 analyzes an image frame from video data comprising a plurality of images of the workstation 402. At 708, the method 700 preprocesses the image frame. For example, the artificial intelligence 216 preprocesses the image frame (e.g., using coloring, data structure conversion, and the like).

At 710, the method 700 detects an object. For example, the artificial intelligence 216 detects at least one object of interest in the image frame. At 712, the method 700 classifies the detected object. For example, the artificial intelligence 216 classified the detected object of interest, as described. At 712, the method 700 identifies a container threshold. For example, the artificial intelligence 216 may identify a container, such as the container 406. The artificial intelligence 216 may identify a threshold, such as the threshold 408, of the container 406, as described. For example, the artificial intelligence 216 may use color filtering, edge detection (e.g., Canny edge detection or other suitable edge detection), line detection (e.g., Hough transformation line detection or other suitable line detection), or a combination thereof to identify the threshold 408. For example, the artificial intelligence 216 may apply a Gaussian filter to smooth the image to remove the noise from the digital image, find the intensity gradients in the image, apply non-maximum suppression to reduce spurious response to edge detection, apply double threshold to determine potential edges in the image, track the edge(s) by hysteresis, and finalize the detection of edge(s) by suppressing all the other edges that are weak and not connected to strong edges.

At 716, the method 700 counts objects using the detected threshold. For example, the artificial intelligence 216 continues to analyze images of the video data provided by the AR device 120 of the workstation 402. The artificial intelligence 216 counts classified objects as they pass the threshold 408 and are placed, by the user of the AR device 120, into the container 406. At 718, the method 700 updates an objects in container list. For example, the box fill detection system 214 may updated the objects in container list to indicate the objects identified by the artificial intelligence 216 as having passed the threshold 408 into the container 406. At 720, the method 700 updates a workstation inventory. For example, the box fill detection system 214 updates a workstation inventory list based on the classified objects in the container 406 (e.g., and no longer in inventory).

At 724, the method 700 updates items in an order count. For example, the RPA system 202 and/or the box fill detection system 214, may update an items in order count displayed on the lenses of the AR device 120 and/or on the order website 204 indicating the classified objects in the container 406. At 726, the method 700 superimposes threshold and detected boxes and any other labels on the image frame and the AR device 120. For example, the box fill detection system 214 may superimpose the threshold 408 on the container 406, the classified objects, and various other labels on the image frame and/or one or more lenses of the AR device 120, as described.

At 728, the method 700 writes the image frame to output video. For example, the box fill detection system 214 may write the image frame, including the superimposed threshold 408, classified objects, and various other labels, to an output video. The output video may be communicated to the order website 204. A pharmacy user may access the output video in order to view fulfillment progress of the pharmacy order. Additionally, or alternatively, the output video may be stored on the accumulated training data 222, as described.

At 730, the method 700 determines whether the items in the container is the same as the expected items in the container. For example, the box fill detection system 214 may compare the items (e.g., classified objects) in the container 406 to the order requirements, as described. If the box fill detection system 214 determines that the items in the container 406 are the same as the expected items indicated by the order requirements, the method 700 ends at 732. If the box fill detection system 214 determines that the items in the container 406 are not the same as the expected items indicated by the order requirements, the method 700 continues at 706.

Figure 8:
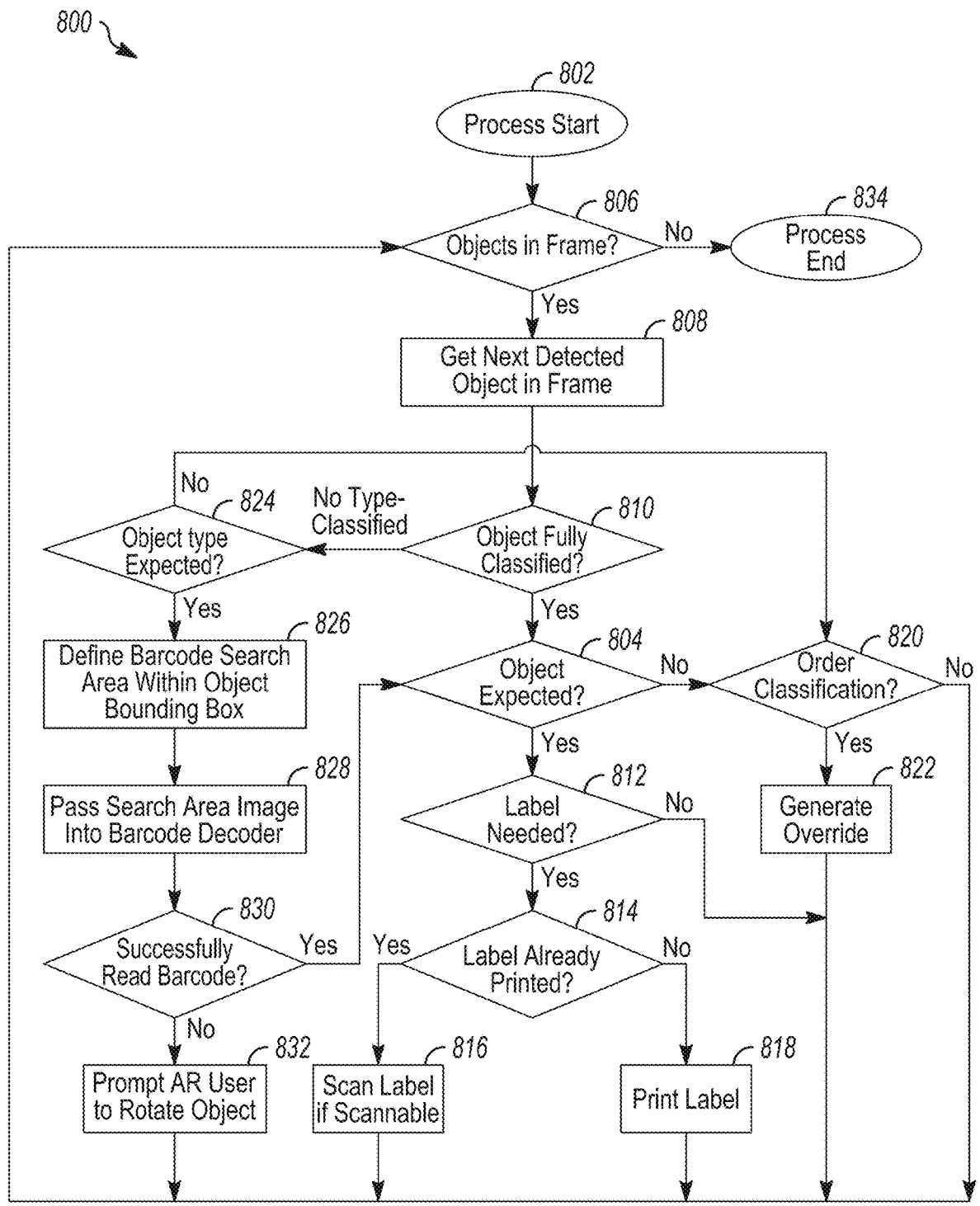
FIG. 8 is a flow diagram generally illustrating an object classification detection method according to the principles of the present disclosure.

FIG. 8 is a flow diagram generally illustrating an object classification detection method 800 according to the principles of the present disclosure. At 802, the method 800 begins. At 804, the method 800 determines whether objects are in the image frame. For example, the artificial intelligence 216 determines whether any objects of interest are in the image frame. If the artificial intelligence 216 determines that there are no objects of interest in the image frame, the method 800 ends at 834. If the artificial intelligence 216 determines that at least one object of interest is in the image frame, the method 800 continues at 806.

At 806, the method 800 gets the next detected object in the image frame. For example, the artificial intelligence 216 detects the objects of interest in the image frame, as described. The box fill detection system 214 retrieves or receives the detected object of interest. At 808, the method 800 determines whether the object is fully classified. For example, the box fill detection system 214 determines whether the artificial intelligence 216 fully classified the object of interest (e.g., specifically classified the object of interest, as described). If the box fill detection system 214 determines that the objects of interest is fully classified, the method 800 continues at 810. If the box fill detection system 214 determines that the object of interest is not fully classified (e.g., the artificial intelligence 216 generically classified the object of interest, as described), the method 800 continues at 824.

At 824, the method 800 determines whether the object type is expected. For example, the box fill detection system 214 determines whether the generic classification of the object of interest includes a type of object that is included in the items corresponding to the order requirements of the pharmacy order. If the box fill detection system 214 determines that the type of object is not expected, the method 800 continues at 820. If the box fill detection system 214 determines that the type of object is expected, the method 800 continues at 826. At 826, the method 800 defines a barcode search area within the object bounding box. For example, the box fill detection system 214 generates the barcode reader box 420, as described. At 828, the method 800 passes a search area image into the barcode decoder. For example, the box fill detection system 214 may use a barcode decoder mechanism to read a barcode on the objects of interest in the barcode reader box 420.

At 830, the method 800 determines whether the barcode was successfully read. For example, the box fill detection system 214 determines whether the barcode decoder successfully read (e.g., decoded) the barcode. If the box fill detection system 214 determines that the barcode decode successfully read the barcode, the method 800 continues at 810. If the box fill detection system 214 determines that the barcode decoder did not successfully read the barcode, the method 800 continues at 832. At 832, the method 800 prompts the user of the AR device 120 to rotate the object. For example, the box fill detection system 214 may provide the indication 414, as described instructing the user of the AR device 120 to reposition the object of interest, such that the barcode is within the barcode reader box 420.

At 810, the method 800 determines whether the object is expected. For example, the box fill detection system 214 determines whether the object (e.g. being fully classified) is an expected item according to the order data corresponding to the pharmacy order. If the box fill detection system 214 determines that the object of interest is an expected object, the method 800 continues at 812. If the box fill detection system 214 determine that the object of interest is not an expected object, the method 800 continues at 820. At 820, the method 800 determines whether the classified object corresponds to fulfillment of a pharmacy order. For example, the box fill detection system 214 determine whether the object of interest corresponds to fulfillment of the pharmacy order or to a workstation restocking. If the box fill detection system 214 determines that the object of interest corresponds to fulfillment of the pharmacy order, the method 800 continues at 822. If the box fill detection system 214 determines that the object of interest corresponds to a workstation restocking, the method 800 continues at 806.

At 822, the method 800 generates an override. For example, the box fill detection system 214 may generate output indicating that the objects of interest was not expected. At 812, the method 800 determines whether a label is needed for the object of interest. For example, the box fill detection system 214 may determine whether a label is required for the object of interest. The box fill detection system 214 may use information indicated in the order requirements to determine whether the object of interest requires a label. If the box fill detection system 214 determines that a label is not required, the method 800 continues at 806. If the box fill detection system 214 determines that a label is required, the method 800 continues at 814.

At 814, the method 800 determines if a label is already printed. For example, the box fill detection system 214 determines whether a label has been printed. For example, the box fill detection system 214 may receive an indication that the label is already printed or the box fill detection system 214, using the artificial intelligence 216, may identify a label in the image frames. If the box fill detection system 214 determines that the label has not been printed, the method 800 continues at 818. If the box fill detection system 214 determines that a label has already been printed, the method 800 continues at 816. At 818, the method 800 prints a label. The method 800 continues at 806. At 816, the method 800 scans the label if capable of being scanned. For example, the box fill detection system 214, using the artificial intelligence 216 or a scanning device, scans the label. The method 800 continues at 806.

Figure 9:
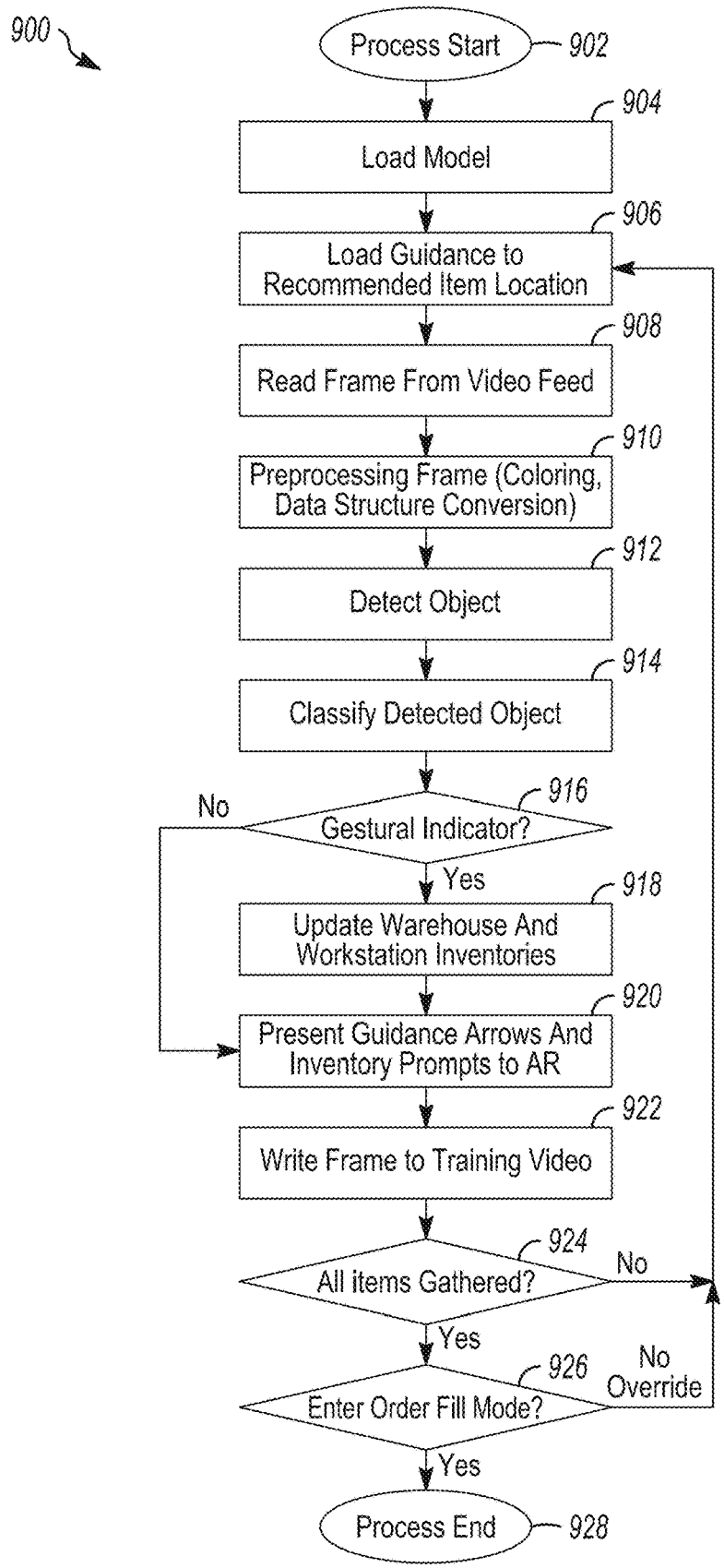
FIG. 9 is a flow diagram generally illustrating a workstation restocking method according to the principles of the present disclosure.

FIG. 9 is a flow diagram generally illustrating a workstation restocking method 900 according to the principles of the present disclosure. At 902, the method 900 begins. At 904, the method 900 loads a model. For example, the artificial intelligence 216 may load a model trained to restock a workstation. At 906, the method 900 loads guidance to recommended item location. For example, the AR hardware system 210 may retrieve information from the warehouse data records 212 including warehouse layout information, warehouse inventory information, inventory location information, other suitable information, or a combination thereof. At 908, the method 900 reads an image frame of the video feed. For example, the AR hardware system 210 reads an image frame of the video feed of the workstation 402, as described.

At 910, the method 900 preprocesses the image frame. For example, the artificial intelligence 216 preprocesses the image frame, as described. At 912, the method 900 detects objects. For example, the artificial intelligence 216 detects objects of interest in the image frame, as described. At 914, the method 900 classifies the detected object. For example, the artificial intelligence 216 classifies the detected object as described.

At 916, the method 900 determines whether the user of the AR device 120 made a gestural indication. For example, the user of the AR device 120 may perform a gesture to indicate that an inventory container or item has been retrieved. The gesture may include one or more motions to retrieve the inventory container or item, a specific gesture, such as a predetermined hand movement, or other suitable gesture. The AR hardware system 210 and/or the artificial intelligence 216 may be configured to recognize the gesture and may provide a visual acknowledgement, such as the visual acknowledgement 308, that the user has retrieved the inventory container or item. If the AR hardware system 210 or the artificial intelligence 216 determines that the user of the AR device 120 made a gestural indication, the method 900 continues at 918. If the AR hardware system 210 or the artificial intelligence 216 determines that the user of the AR device 120 did not make a gestural indication, the method 900 continues at 920.

At 918, the method 900 updates the warehouse and workstation inventories. For example, the AR hardware system 210 may update the warehouse inventory list and/or workstation inventory list, as described. At 920, the method 900 presents guidance arrows and inventory prompts to the AR device 120. For example, the AR hardware system 210 may provide the guided access to one or more lenses of the AR device 120, as described. At 922, the method 900 writes the image frame to a training video. For example, the AR hardware system 210 may write the image frame to a training video. The AR hardware system 210 may store the training video in the accumulated training data 222, as described.

At 924, the method 900 determines whether all items have been gathered. For example, the AR hardware system 210 may compare the items on the workstation inventory list with the items required to fulfill the pharmacy order indicated by the order requirements. If the AR hardware system 210 determines that the items on the workstation inventory list are the same as the items required to fulfill the pharmacy order, the method 900 continues at 926. If the AR hardware system 210 determines that the items on the workstation inventory list are not the same as the items required to fulfill the pharmacy order, the method 900 continue at 906.

At 926, the method 900 determines whether to enter an order fill mode. For example, the AR hardware system 210 determine whether to enter an order fill mode base on input from the user of the AR device 120 or based on the items on the workstation inventory list being the same as the items required to fulfill the pharmacy order. If the AR hardware system 210 determines not to enter the order fill mode, the method 900 continues at 906. If the AR hardware system 210 determines to enter the order fill mode, the method ends at 928.

Figure 10:
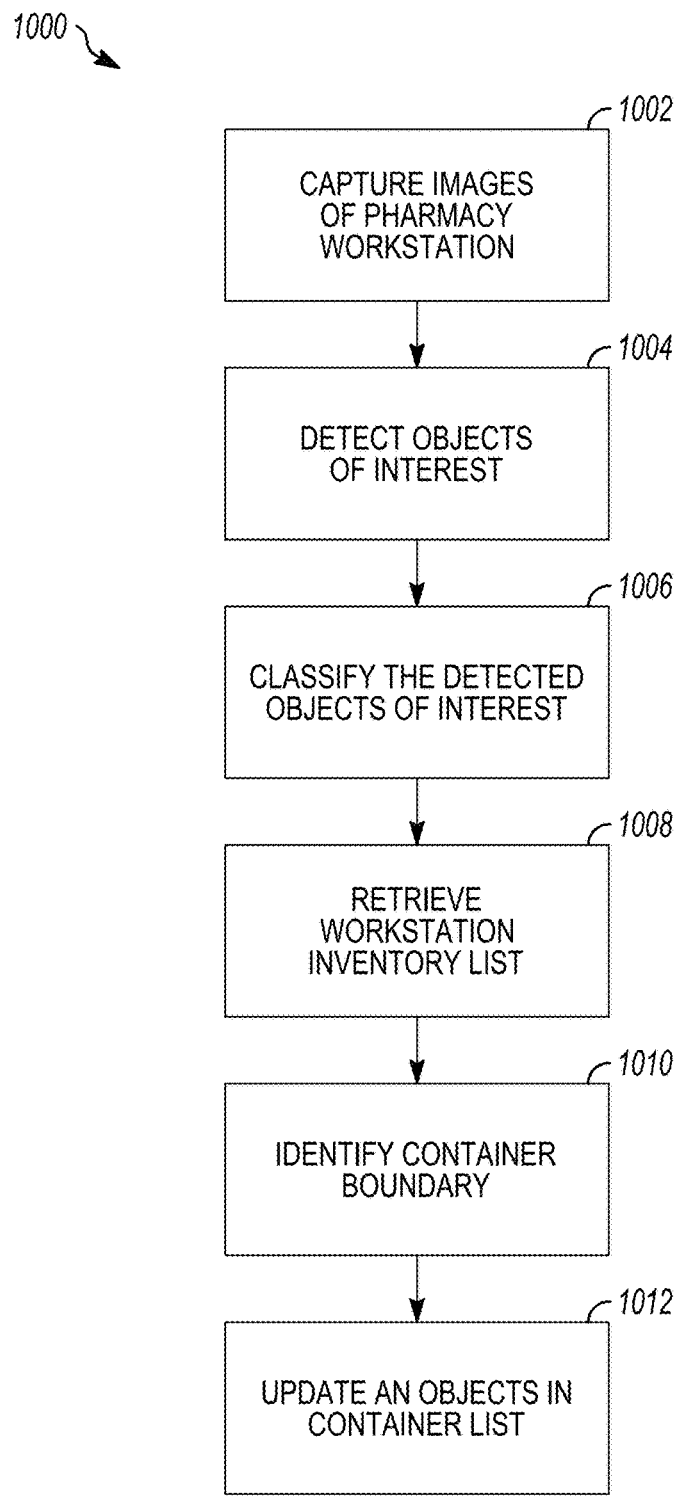
FIG. 10 is a flow diagram generally illustrating an alternative pharmacy order fill method according to the principles of the present disclosure.

FIG. 10 is a flow diagram generally illustrating an alternative pharmacy order fill method 1000 according to the principles of the present disclosure. At 1002, the method 1000 captures images of the pharmacy workstation. For example, the AR device 120 captures video data include a plurality of images of the workstation 402. At 1004, the method 1000 detects objects of interest in the plurality of images. For example, the artificial intelligence 216 detects objects of interest in the plurality of images, as described. At 1006, the method 1000 classifies the detected objects of interest. For example, the artificial intelligence 216 classifies the detected objects of interest. At 1008, the method 1000 retrieves a workstation inventory list. For example, the box fill detection system 214 and/or the AR hardware system 210 retrieves the workstation inventory list, as described.

At 1010, the method 1000 identified a container boundary. For example, the box fill detection system 214, using the artificial intelligence 216, detects the threshold 408 of the container 406. At 1012, the method 1000 updates an objects in container list. For example, the artificial intelligence 216 identifies objects passing the threshold 408, as described. The box fill detection system 214 updates the objects in container list based on the objects identified by the artificial intelligence 216 having passed the threshold.

In some embodiments, a method for fulfilling a pharmacy order includes capturing, by an image-capturing device, a one or more images of at least a portion of a pharmacy workstation. The method also includes identifying, by a processor in communication with the image capturing device, objects of interest in a first image of the one or more images and classifying, by the processor, the detected objects of interest using a convolutional neural network associated with the processor. The method also includes updating, by the processor, a workstation inventory list based on the classification of the detected objects of interest and identifying, by the processor, a boundary defining an opening of a container in a second image of the one or more images. The method also includes updating, by the processor, an objects in container list based on a determination that at least one of the classified objects passed the boundary.

In some embodiments, identifying, by the processor, the boundary defining the opening of the container includes using color filtering. In some embodiments, identifying, by the processor, the boundary defining the opening of the container includes using Canny edge detection. In some embodiments, identifying, by the processor, the boundary defining the opening of the container includes using Hough transform line detection. In some embodiments, classifying, by the processor, the detected objects of interest using the convolutional neural network associated with the processor includes identifying barcodes on at least some of the objects using the convolutional neural network. In some embodiments, the method also includes providing by the processor to a display device, an indication corresponding to the objects in container list. In some embodiments, the method also includes determining, by the processor, whether the objects in container list is the same as an expected objects list. In some embodiments, the method also includes indicating, by the processor on a display device, that the pharmacy order is fulfilled based on a determination that objects in container list is the same as the expected objects list.

In some embodiments, an augmented reality apparatus for fulfilling a pharmacy order includes an image-capturing device, a processor, and a display device. The image-capturing device is configured to capture video data that includes a one or more images of at least a portion of a pharmacy workstation. The processor in communication with at least one memory that includes instructions that, when executed by the processor, cause the processor to: read a first image of the one or more images of the video data; identify objects of interest in the first image; classify the detected objects of interest using a convolutional neural network; identify a boundary defining an opening of a container in a second image of the one or more images; update an objects in container list based on a determination that at least one of the classified objects passed the boundary; and generate information corresponding to the pharmacy order based on, at least, the objects in container list. The display device is configured to display the information.

In some embodiments, the instructions further cause the processor to identify the boundary defining the opening of the container includes using color filtering. In some embodiments, the instructions further cause the processor to identify the boundary defining the opening of the container includes using Canny edge detection. In some embodiments, the instructions further cause the processor to identify the boundary defining the opening of the container includes using Hough transform line detection. In some embodiments, the instructions further cause the processor to classifies the detected objects of interest by at least identifying barcodes on at least some of the objects using the convolutional neural network. In some embodiments, the instructions further cause the processor to update the workstation inventory list based on the determination that at least one of the classified objects passed the boundary. In some embodiments, the information includes an indication corresponding objects in the objects in container list. In some embodiments, the instructions further cause the processor to determine whether the objects in container list is the same as an expected objects list. In some embodiments, the information includes an indication that the pharmacy order is fulfilled based on a determination that objects in container list is the same as the expected objects list.

In some embodiments, a system for fulfilling a pharmacy order includes a wearable augmented reality device and a convolutional neural network. The wearable augmented reality device is configured to: capture video data that includes a one or more images of at least a portion of a pharmacy workstation; identify objects of interest in the one or more images; and identify a boundary defining an opening of a container in the one or more images. The convolutional neural network is configured to classify the objects of interest identified by the wearable augmented reality device, wherein the wearable augmented reality device identifies, in the one or more images, classified objects of interest that pass the boundary of the container and provides, to a wearer of the wearable augmented reality device, information corresponding to the pharmacy order in response to identifying classified objects of interest that pass the boundary of the container.

In some embodiments, the wearable augmented reality device is further configured to determine whether the pharmacy order is fulfilled in response to identifying classified objects that pass the boundary of the container, wherein the information includes an indication that the pharmacy order is fulfilled.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The word "example" is used herein to mean serving as an example, instance, or illustration. Any aspect or design described herein as "example" is not necessarily to be construed as preferred or advantageous over other aspects or designs. Rather, use of the word "example" is intended to present concepts in a concrete fashion. As used in this application, the term "or" is intended to mean an inclusive "or" rather than an exclusive "or." That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an implementation" or "one implementation" throughout is not intended to mean the same embodiment or implementation unless described as such.

Implementations the systems, algorithms, methods, instructions, etc., described herein can be realized in hardware, software, or any combination thereof. The hardware can include, for example, computers, intellectual property (IP) cores, application-specific integrated circuits (ASICs), programmable logic arrays, optical processors, programmable logic controllers, microcode, microcontrollers, servers, microprocessors, digital signal processors, or any other suitable circuit. In the claims, the term "processor" should be understood as encompassing any of the foregoing hardware, either singly or in combination. The terms "signal" and "data" are used interchangeably.

As used herein, the term module can include a packaged functional hardware unit designed for use with other components, a set of instructions executable by a controller (e.g., a processor executing software or firmware), processing circuitry configured to perform a particular function, and a self-contained hardware or software component that interfaces with a larger system. For example, a module can include an application specific integrated circuit (ASIC), a Field Programmable Gate Array (FPGA), a circuit, digital logic circuit, an analog circuit, a combination of discrete circuits, gates, and other types of hardware or combination thereof. In other embodiments, a module can include memory that stores instructions executable by a controller to implement a feature of the module.

Further, in one aspect, for example, systems described herein can be implemented using a general-purpose computer or general-purpose processor with a computer program that, when executed, carries out any of the respective methods, algorithms, and/or instructions described herein. In addition, or alternatively, for example, a special purpose computer/processor can be utilized which can contain other hardware for carrying out any of the methods, algorithms, or instructions described herein.

Further, all or a portion of implementations of the present disclosure can take the form of a computer program product accessible from, for example, a computer-usable or computer-readable medium. A computer-usable or computer-readable medium can be any device that can, for example, tangibly contain, store, communicate, or transport the program for use by or in connection with any processor. The medium can be, for example, an electronic, magnetic, optical, electromagnetic, or a semiconductor device. Other suitable mediums are also available.

The above-described embodiments, implementations, and aspects have been described in order to allow easy understanding of the present invention and do not limit the present invention. On the contrary, the invention is intended to cover various modifications and equivalent arrangements included within the scope of the appended claims, which scope is to be accorded the broadest interpretation to encompass all such modifications and equivalent structure as is permitted under the law.

What is claimed is:

1. A method for fulfilling a pharmacy order, the method comprising:
    capturing, by an image-capturing device of a wearable augmented reality device, a one or more images of at least a portion of a pharmacy workstation;
    retrieving, using a processor of the wearable augmented reality device, pharmacy order information indicating at least one pharmacy item corresponding to a pharmacy order of a pharmacy customer;
    identifying, by the processor using the image-capturing device of the wearable augmented reality device, objects of interest in a first image of the one or more images captured by the image-capturing device of the wearable augmented reality device, the objects of interest corresponding to at least the at least one pharmacy item;
    classifying, by the processor, the detected objects of interest;
    identifying, by the processor using the image-capturing device, a virtual boundary defining an opening of a container in a second image of the one or more images;
    superimposing, on the display of the wearable augmented reality device, a threshold that defines a virtual opening bound by the virtual boundary on the container;
    counting detected objects of interest passing the threshold into the container;
    updating, by the processor, an objects in container list based on a determination that at least one of the classified objects passed the threshold;
    displaying, on the display of the wearable augmented reality device, the objects in container list.

2. The method of claim 1, wherein identifying, by the processor, the virtual boundary defining the opening of the container includes using color filtering.

3. The method of claim 1, wherein identifying, by the processor, the virtual boundary defining the opening of the container includes using Canny edge detection.

4. The method of claim 1, wherein identifying, by the processor, the virtual boundary defining the opening of the container includes using Hough transform line detection.

5. The method of claim 1, wherein classifying, by the processor, the detected objects of interest includes using a convolutional neural network associated with the processor to identify barcodes on at least some of the objects using the convolutional neural network.

6. The method of claim 1, further comprising updating, by the processor, a workstation inventory list based on the determination that at least one of the classified objects passed the threshold.

7. The method of claim 1, further comprising, providing by the processor to a display device, an indication corresponding to the objects in container list.

8. The method of claim 1, further comprising determining, by the processor, whether the objects in container list is the same as an expected objects list.

9. The method of claim 8, further comprising indicating, by the processor on a display device, that the pharmacy order is fulfilled based on a determination that objects in container list is the same as the expected objects list.

10. The method of claim 1, further comprising generating, by the processor using the image-capturing device, at least one image frame that includes at least the container and at least one object of interest proximate the virtual boundary.

11. The method of claim 10, further comprising, superimposing, by the processor, on the container in the at least one image frame, the threshold that defines the virtual boundary.

12. The method of claim 11, further comprising, generating, by the processor, an output video using the at least one image frame.

13. The method of claim 12, further comprising transmitting, by the processor, the output video to a user interface, wherein the user interface is configured to allow the pharmacy customer to access the output video.

14. The method of claim 1, further comprising, indicating, by the processor on the display of the wearable augmented reality device, to the wearer of the augmented reality device, the objects of interest on the pharmacy workstation.

15. The method of claim 1, wherein displaying, on the display of the wearable augmented reality device, includes displaying the objects in container list simultaneously with the threshold.

16. The method of claim 1, wherein superimposing the threshold includes moving the threshold on the wearable device to match a physical location of the container.

17. An augmented reality apparatus for fulfilling a pharmacy order, the augmented reality apparatus comprising:
    an image-capturing device configured to capture video data that includes a one or more images of at least a portion of a pharmacy workstation;
    a processor in communication with at least one memory that includes instructions that, when executed by the processor, cause the processor to:
        retrieve pharmacy order information indicating at least one pharmacy item corresponding to the pharmacy order, the pharmacy order corresponding to a pharmacy customer;
        read a first image of the one or more images of the video data;

identify objects of interest in the first image, the objects of interest corresponding to at least the at least one pharmacy item;

classify the detected objects of interest;

identify a virtual boundary defining an opening of a container in a second image of the one or more images;

superimpose, on the display device, a threshold that defines a virtual opening bound by the virtual boundary on the container;

count detected objects of interest passing the threshold into the container;

update an objects in container list based on a determination that at least one of the classified objects passed the threshold; and generate information corresponding to the pharmacy order based on, at least, the objects in container list; and a display device configured to display the information, the information indicating, at least, the objects in container list.

18. The augmented reality apparatus of claim 17, wherein the instructions further cause the processor to identify the virtual boundary defining the opening of the container includes using color filtering.

19. The augmented reality apparatus of claim 17, wherein the instructions further cause the processor to identify the virtual boundary defining the opening of the container includes using Canny edge detection.

20. The augmented reality apparatus of claim 17, wherein the instructions further cause the processor to identify the virtual boundary defining the opening of the container includes using Hough transform line detection.

21. The augmented reality apparatus of claim 17, wherein the instructions further cause the processor to classifies the detected objects of interest by at least identifying barcodes on at least some of the objects using a convolutional neural network.

22. The augmented reality apparatus of claim 17, wherein the instructions further cause the processor to update a workstation inventory list based on the determination that at least one of the classified objects passed the threshold.

23. The augmented reality apparatus of claim 17, wherein the information includes an indication corresponding objects in the objects in container list.

24. The augmented reality apparatus of claim 17, wherein the instructions further cause the processor to determine whether the objects in container list is the same as an expected objects list.

25. The augmented reality apparatus of claim 24, wherein the information includes an indication that the pharmacy order is fulfilled based on a determination that objects in container list is the same as the expected objects list.

26. A system for fulfilling a pharmacy order, the system comprising:

a wearable augmented reality device configured to:
capture video data that includes a one or more images of at least a portion of a pharmacy workstation;
retrieve pharmacy order information indicating at least one pharmacy item corresponding to the pharmacy order, the pharmacy order corresponding to a pharmacy customer;
identify objects of interest in the one or more images, the objects of interest corresponding to at least the at least one pharmacy item; and
identify a virtual boundary defining an opening of a container in the one or more images;

a processor configured to classify the objects of interest identified by the wearable augmented reality device, wherein the wearable augmented reality device:
identifies, in the one or more images, classified objects of interest that pass the virtual boundary of the container;
superimposes, on a display of the wearable augmented reality device, a threshold that defines a virtual opening bound by the virtual boundary on the container;
counts classified objects of interest that pass the threshold into the container; and
provides, to a wearer of the wearable augmented reality device on the display of the wearable augmented reality device, information corresponding to the pharmacy order in response to counting classified objects of interest that pass the virtual opening of the container.

27. The system of claim 26, wherein the wearable augmented reality device is further configured to determine whether the pharmacy order is fulfilled in response to counting classified objects that pass the virtual boundary of the container, wherein the information includes an indication that the pharmacy order is fulfilled.

* * * * *